US011013495B2

(12) United States Patent
Hwang et al.

(10) Patent No.: US 11,013,495 B2
(45) Date of Patent: May 25, 2021

(54) METHOD AND APPARATUS FOR REGISTERING MEDICAL IMAGES

(71) Applicants: SAMSUNG ELECTRONICS CO., LTD., Suwon-si (KR); SAMSUNG LIFE PUBLIC WELFARE FOUNDATION, Seoul (KR)

(72) Inventors: Youngkyoo Hwang, Seoul (KR); Jungbae Kim, Seoul (KR); Youngtaek Oh, Seoul (KR); Wonchul Bang, Seongnam-si (KR); Minwoo Lee, Seoul (KR)

(73) Assignees: SAMSUNG ELECTRONICS CO., LTD., Suwon-si (KR); SAMSUNG LIFE PUBLIC WELFARE FOUNDATION., Seoul (KR)

(*) Notice: Subject to any disclaimer, the term of this patent is extended or adjusted under 35 U.S.C. 154(b) by 886 days.

(21) Appl. No.: 14/477,157

(22) Filed: Sep. 4, 2014

(65) Prior Publication Data
US 2015/0065859 A1 Mar. 5, 2015

(30) Foreign Application Priority Data
Sep. 4, 2013 (KR) .......................... 10-2013-0106309

(51) Int. Cl.
*A61B 8/08* (2006.01)
*A61B 6/00* (2006.01)
(Continued)

(52) U.S. Cl.
CPC .......... *A61B 8/5261* (2013.01); *A61B 5/0035* (2013.01); *A61B 5/055* (2013.01);
(Continued)

(58) Field of Classification Search
CPC ..................... G06T 7/143; G06T 7/187; G06T 2207/10136; G06T 7/00;
(Continued)

(56) References Cited

U.S. PATENT DOCUMENTS

| 8,170,347 B2 | 5/2012 | Ancelin |
| 8,238,625 B2 | 8/2012 | Strommer et al. |

(Continued)

FOREIGN PATENT DOCUMENTS

| JP | 2012-245351 A | 12/2012 |
| KR | 10-2009-0127101 A | 12/2009 |

(Continued)

OTHER PUBLICATIONS

Communication dated Jun. 24, 2015, issued by the European Patent Office in counterpart European Application No. 14183504.1.

(Continued)

*Primary Examiner* — James M Kish
(74) *Attorney, Agent, or Firm* — Sughrue Mion, PLLC

(57) ABSTRACT

A method for registering medical images of different types, includes: receiving a selection of at least one point in a first medical image that is acquired in non-real time; extracting, from the first medical image, a first anatomic object which includes the selected point and a second anatomic object which is adjacent to the selected point; extracting, from a second medical image that is acquired in real time, a third anatomic object which corresponds to the first anatomic object and a fourth anatomic object which corresponds to the second anatomic object; and registering the first medical image and the second medical image based on a geometric relation between the first, second, third, and fourth anatomic objects.

23 Claims, 16 Drawing Sheets
(6 of 16 Drawing Sheet(s) Filed in Color)

(51) Int. Cl.
  *A61B 6/03* (2006.01)
  *A61B 5/00* (2006.01)
  *A61B 5/055* (2006.01)
  *G06T 7/11* (2017.01)
  *G06T 7/143* (2017.01)
  *G06T 7/187* (2017.01)
  *G06T 7/136* (2017.01)
  *G06T 7/33* (2017.01)

(52) U.S. Cl.
  CPC .............. *A61B 6/032* (2013.01); *A61B 6/037* (2013.01); *A61B 6/5247* (2013.01); *G06T 7/11* (2017.01); *G06T 7/136* (2017.01); *G06T 7/143* (2017.01); *G06T 7/187* (2017.01); *G06T 7/33* (2017.01); *G06T 7/337* (2017.01); *G06T 2207/10072* (2013.01); *G06T 2207/10136* (2013.01); *G06T 2207/20101* (2013.01); *G06T 2207/20221* (2013.01); *G06T 2207/30056* (2013.01); *G06T 2207/30101* (2013.01)

(58) Field of Classification Search
  CPC ....... G06T 2207/30056; G06T 7/30–38; G06T 2207/30101; A61B 8/08; A61B 6/03; A61B 6/00; A61B 5/0035; A61B 8/5261; G06K 9/46; G01R 33/48
  See application file for complete search history.

(56) References Cited

U.S. PATENT DOCUMENTS

| | | | |
|---|---|---|---|
| 8,290,303 B2 | 10/2012 | Washburn et al. | |
| 8,345,943 B2 | 1/2013 | Neemuchwala et al. | |
| 8,369,597 B2 | 2/2013 | Hyun et al. | |
| 8,447,383 B2 | 5/2013 | Hyun et al. | |
| 8,606,045 B2 | 12/2013 | Lee | |
| 9,563,949 B2 * | 2/2017 | Hwang | G06T 7/33 |
| 2003/0233039 A1 * | 12/2003 | Shao | G06T 7/20 |
| | | | 600/407 |
| 2005/0251028 A1 * | 11/2005 | Boese | |
| 2008/0085042 A1 * | 4/2008 | Trofimov | A61B 5/042 |
| | | | 382/128 |
| 2008/0247622 A1 * | 10/2008 | Aylward | A61B 90/36 |
| | | | 382/131 |
| 2009/0175557 A1 * | 7/2009 | Lankoande | G01S 13/9035 |
| | | | 382/275 |
| 2009/0306507 A1 * | 12/2009 | Hyun | G06T 7/11 |
| | | | 600/443 |
| 2009/0306509 A1 | 12/2009 | Pedersen et al. | |
| 2010/0067755 A1 | 3/2010 | Chan et al. | |
| 2010/0135546 A1 | 6/2010 | Cziria | |
| 2011/0243401 A1 * | 10/2011 | Zabair | G06K 9/00 |
| | | | 382/128 |
| 2014/0193053 A1 * | 7/2014 | Kadoury | G06T 11/008 |
| | | | 382/131 |
| 2016/0086326 A1 * | 3/2016 | Raschke | G06T 7/0012 |
| | | | 382/131 |

FOREIGN PATENT DOCUMENTS

| | | | | |
|---|---|---|---|---|
| KR | 10-2010-0062889 A | 6/2010 | | |
| KR | 10-2011-0013738 A | 2/2011 | | |
| KR | 10-1121353 A | 3/2012 | | |
| WO | WO 2011/161684 A2 * | 12/2011 | ............. | A61B 19/00 |
| WO | WO 2012/117381 A1 * | 9/2012 | ............. | A61B 19/00 |

OTHER PUBLICATIONS

Adams R et al: "Seeded region growing", IEEE Transactions on Pattern Analysis and Machine Intelligence, IEEE Computer Society, USA, vol. 16, No. 6, Jun. 1, 1994 (Jun. 1, 1994), pp. 641-647, XP002215479.

Tsukasa Shindo et al: "3D Visualization of Liver and Its Vascular Structures and Surgical Planning System Surgical Simulation", Computer Sciences and Convergence Information Technology (ICCIT), 2011 6th International Conference on, IEEE, Nov. 29, 2011 (Nov. 29, 2011), pp. 939-944, XP032257764.

Woo Hyun Nam et al: "Automatic registration between 3D intra-operative ultrasound and pre-operative CT images of the liver based on robust edge matching", Physics in Medicine and Biology, Institute of Physics Publishing, Bristol GB, vol. 57, No. 1, Nov. 29, 2011 (Nov. 29, 2011), pp. 69-91, XP020216220.

Communication dated Oct. 27, 2020, issued by the Korean Intellectual Property Office in Korean Patent Application No. 10-2013-0106309.

* cited by examiner

METHOD AND APPARATUS FOR REGISTERING MEDICAL IMAGES

CROSS-REFERENCE TO RELATED APPLICATIONS

This application claims priority from Korean Patent Application No. 10-2013-0106309, filed on Sep. 4, 2013 in the Korean Intellectual Property Office, the disclosure of which is incorporated herein by reference in its entirety.

BACKGROUND

1. Field

Exemplary embodiments relate to methods and apparatuses for registering medical images of different types.

2. Description of the Related Art

Recently, since high-resolution medical images may be obtained and medical instruments may be precisely operated due to the developments of medical technologies, a method has been developed to perform a medical treatment while observing the inside of a body of a patient by directly inserting a catheter or a medical needle into a blood vessel or a desired body region after making a small hole in the skin of the patient without making in the body a cut for exposing a treatment region. This method is referred to as an image-based surgical operation, an interventional image-based surgical operation, or a mediate image-based surgical operation. An operator detects the position of an organ or the occurrence of a disease based on an image. In addition, since a patient breathes or moves during a surgical operation, the operator should detect a change in the position of the organ caused by breathing or movement of the patient. Therefore, the operator should perform a surgical operation by rapidly and accurately detecting the breathing or movement of the patient based on a real-time image. However, it is not easy to detect, in real time with the naked eye, the shape of an organ or the occurrence of a disease. Unlike an ultrasound image, a magnetic resonance (MR) or computed tomography (CT) image enables the operator to clearly identify an organ and a disease. However, since an MR or CT image may not be acquired in real time during a surgical operation, the MR or CT image may not reflect the breathing and movement of a patient during the surgical operation.

SUMMARY

Provided are methods and apparatuses for rapidly and accurately registering a medical image that is acquired in non-real time and a real-time medical image that is acquired in real time.

Additional aspects will be set forth in part in the description which follows and, in part, will be apparent from the description, or may be learned by practice of the presented exemplary embodiments.

According to an aspect of one or more exemplary embodiments, a method for registering medical images of different types includes: receiving a selection of at least one point from within a first medical image that is acquired in non-real time; extracting, from the first medical image, a first anatomic object which includes the selected point and a second anatomic object which is adjacent to the selected point; extracting, from a second medical image that is acquired in real time, a third anatomic object which corresponds to the first anatomic object and a fourth anatomic object which corresponds to the second anatomic object; and registering the first medical image and the second medical image based on a geometric relation between the first, second, third, and fourth anatomic objects.

According to another aspect of one or more exemplary embodiments, a non-transitory computer-readable recording medium stores a program which, when executed by a computer, performs the above method.

According to another aspect one or more exemplary embodiments, an apparatus for registering medical images of different types includes: a storage device configured to store a first medical image that is acquired in non-real time; a user interface configured to output the stored first medical image and to receive a selection of at least one point from within the first medical image; a medical image acquisition device configured to acquire, in real time, a second medical image of a different type from the first medical image; and an image processor configured to extract, from the first medical image, a first anatomic object which includes the selected point and a second anatomic object which is adjacent to the selected point; to extract, from the second medical image, a third anatomic object which corresponds to the first anatomic object and a fourth anatomic object which corresponds to the second anatomic object; and to register the first medical image and the second medical image based on a geometric relation between the first, second, third, and fourth anatomic objects.

BRIEF DESCRIPTION OF THE DRAWINGS

The patent or application file contains at least one drawing executed in color. Copies of this patent or patent application publication with color drawing(s) will be provided by the Office upon request and payment of the necessary fee. These and/or other aspects will become apparent and more readily appreciated from the following description of exemplary embodiments, taken in conjunction with the accompanying drawings in which.

DETAILED DESCRIPTION

Figure 1:
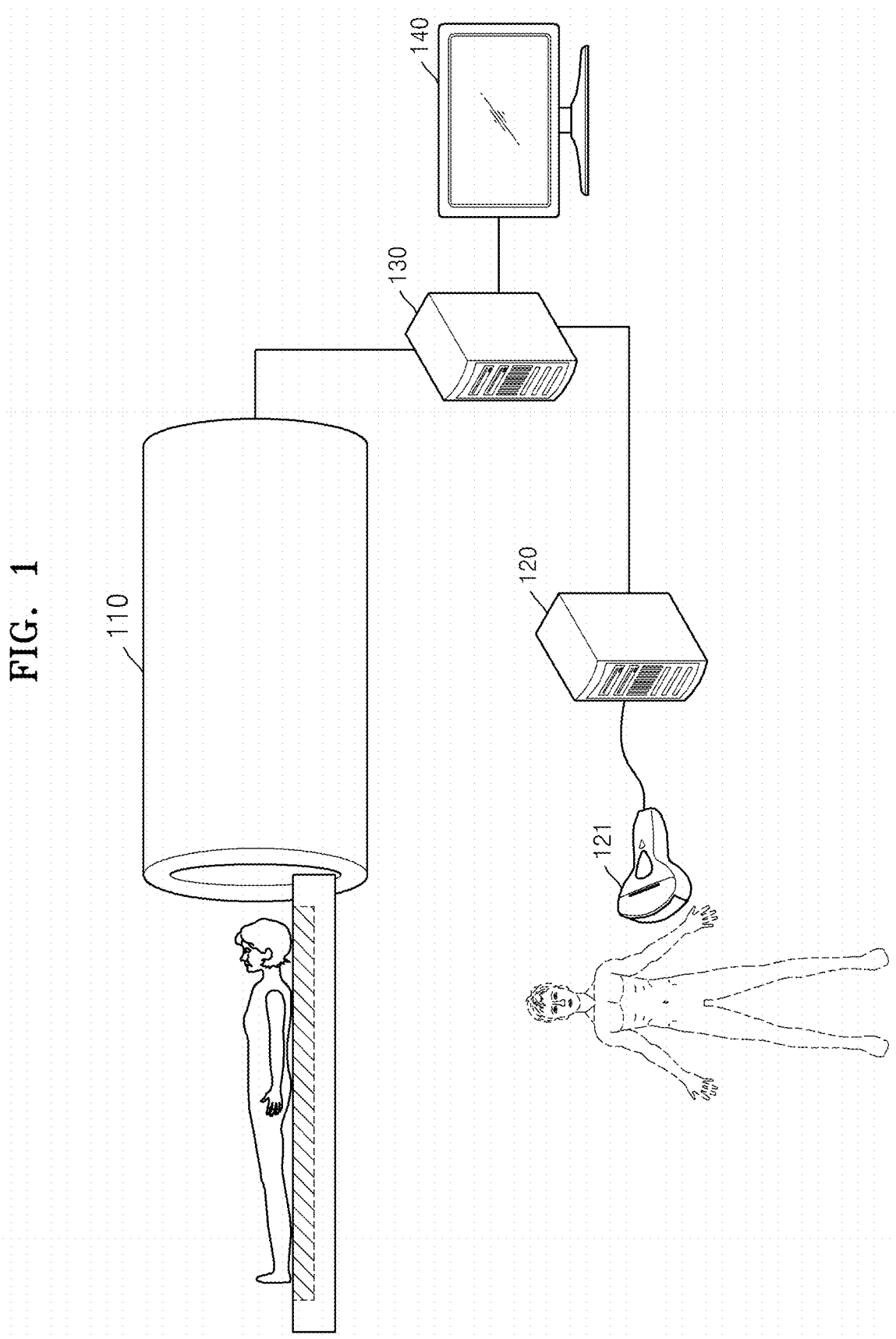
FIG. 1 is a diagram which illustrates a system, according to an exemplary embodiment.

Reference will now be made in detail to exemplary embodiments, examples of which are illustrated in the accompanying drawings, wherein like reference numerals refer to the like elements throughout. In this regard, the present exemplary embodiments may have different forms and should not be construed as being limited to the descriptions set forth herein. Accordingly, the exemplary embodiments are merely described below, by referring to the figures, to explain aspects of the present description. As used herein, the term "and/or" includes any and all combinations of one or more of the associated listed items. Expressions such as "at least one of," when preceding a list of elements, modify the entire list of elements and do not modify the individual elements of the list.

Hereinafter, exemplary embodiments will be described in detail with reference to the accompanying drawings.

FIG. 1 illustrates a system, according to an exemplary embodiment. Referring to FIG. 1, the system includes a first medical device 110, a second medical device 120, a medical image registering apparatus 130, and an image display device 140.

The first medical device 110 and the second medical device 120 respectively generate a first medical image and a second medical image and transmit the first medical image and the second medical image to the medical image registering apparatus 130. The first medical image and the second medical image are of different types. In particular, the first medical image and the second medical image are different from each other in terms of the generation modes and principles. The medical image registering apparatus 130 acquires the first medical image and the second medical image and registers the first medical image and the second medical image. The image registered by the medical image registering apparatus 130 is displayed on the image display device 140.

In the exemplary embodiment illustrated in FIG. 1, the second medical device 120, the medical image registering apparatus 130, and the image display device 140 are configured as independent devices. However, in another exemplary embodiment, the second medical device 120, the medical image registering apparatus 130, and the image display device 140 may be implemented in conjunction with each other as a single apparatus.

The first medical device 110 generates, in non-real time, a first medical image which relates to a volume of interest (VOI) of a target object. Due to the non-real-time characteristics of the first medical device 110, the first medical image may be generated in advance of a medical operation.

For example, the first medical device 110 may include any one of a computed tomography (CT) imaging device, a magnetic resonance (MR) imaging device, an X-ray imaging device, a single positron emission computed tomography (SPECT) imaging device, and a positron emission tomography (PET) imaging device. In the following description, for the convenience of description, it is assumed that the first medical image is an MR or CT image; however, exemplary embodiments are not limited thereto.

In the case of a CT or MR image generated by the first medical device 110, the position of an organ or a disease may be clearly identified. However, when a patient breathes or moves during a surgical operation, an organ may be modified or displaced, and the CT or MR image may not reflect the modification or displacement of the organ caused by the movement of the patient in real time.

In the case of the CT image, because tomography is performed by using radiation, and thus the patient and the operator may be exposed to radioactivity for a relatively long period of time, short-time tomography is recommended. Further, in the case of the MR image, a relatively long time may be required in order to photograph an image. Therefore, the first medical device 110 may not output an image in real time. In general, a CT image is captured in a state where a patient temporarily stops breathing, such as, for example, in a state of maximum inhalation.

The second medical device 120 provides, in real time, a second medical image which relates to the VOI of a target object. For example, when the organ is modified or displaced by a physical activity of the target object, a corresponding change appears in real time in the second medical image. However, in the case of the second medical image, all organs or diseases may not be clearly observed, and the modification or displacement of the organ may be difficult to detect only via the second medical image, as will be described below.

According to an exemplary embodiment, the second medical device 120 may include an ultrasonography machine that generates an image in real time during an ongoing medical operation. However, the second medical device 120 may include other medical devices, such as, for example, an optical coherence tomography (OCT) apparatus that provides an image in real time, and exemplary embodiments are not limited to the ultrasonography machine.

The second medical device 120 generates an ultrasound image by transmitting an ultrasound signal onto a region of interest by a probe 121 and detecting a reflected ultrasound signal. In general, the probe 121 includes a piezoelectric transducer. When an ultrasound wave which has a frequency of between several MHz and hundreds of MHz is transmitted from the probe 121 to a certain region inside the body of the patient, the ultrasound wave is partially reflected from layers between any of various other tissues. The ultrasound wave is reflected from anatomic objects, for which a corresponding density may vary, such as, for example, blood cells inside blood plasma and small tissues (structures) inside organs.

The reflected ultrasound waves cause the piezoelectric transducer of the probe 121 to vibrate, and the piezoelectric transducer outputs electrical pulses in response to vibrations of the piezoelectric transducer. The electrical pulses are converted into an image. When the anatomic objects have different ultrasound reflection characteristics, the respective anatomic objects correspond to different brightness values in a B-mode ultrasound image.

The medical images captured by the first medical device 110 and the second medical device 120 may be three-dimensional (3D) images that are generated by accumulating two-dimensional (2D) sections. For example, the first medical device 110 captures a plurality of sectional images by changing the position and orientation of a sectional image. When the sectional images are accumulated, image data of a 3D volume representing a certain region of the body of the patient in a 3D manner may be generated. A method for generating image data of a 3D volume by accumulating sectional images is referred to as a multiplanar reconstruction method. In the following description, it is assumed that all of the images captured by the first medical device 110 and the second medical device 120 are 3D images. In addition, either or both of the first medical image and/or the second medical image may be a contrast-enhanced image in order to increase the brightness of an organ of interest of the patient.

Conversely, in the case of the medical images obtained by the second medical device 120, for example, ultrasound images, the images may be obtained in real time, but it may be difficult to identify the contour of an organ, an internal structure, or a disease because a noise may be contained therein. Because a disease and a peripheral tissue often have similar ultrasound characteristics, the contrast of brightness between the boundary between the disease and the peripheral tissue, that is, the edge contrast of the object, may be relatively low. Further, noise and artifacts are often present due to the interference and scattering of an ultrasound wave. As a result, the ultrasound medical image may be acquired more rapidly than the MR or CT image, but the identifiable organ and disease may not be clearly identified from the peripheral tissue in the MR or medical image because a signal-to-noise ratio (SNR) and the edge contrast of the object are low.

For example, all of the anatomic objects in the first medical image may not be identifiable in the second medical image that is acquired at a low resolution in real time. For example, in an ultrasound image of a liver region, anatomic information which relates to the shape of a liver is often not identifiable due to mixing with noise. Instead, because the blood vessels of the liver appear darker than the background in the ultrasound image, the blood vessel structure of the liver may be detected based on the shade of the ultrasound image. In the ultrasound image, the position of the liver may be estimated based on the blood vessel structure of the liver. Further, the ultrasound image and the MR or CT image may be registered by comparing the blood vessel structures of the liver extracted from the MR or CT image. However, in the case of a liver cancer patient or a cirrhosis patient, the blood vessel structure of a liver may be difficult to identify in the ultrasound image due to the necrosis of a liver tissue. As a result, the ultrasound image of a liver cancer patient or a cirrhosis patient may be difficult to register with the MR or CT image.

The medical image registering apparatus 130 registers the first medical image acquired from the first medical device 110 and the second medical image acquired from the second medical device 120. The registering of the medical images includes mapping coordinate systems used by the first medical device 110 and the second medical device 120. For example, the first medical device 110 and the second medical device 120 may use a coordinate system based on Digital Imaging and Communication in Medicine (DICOM).

The medical image registering apparatus 130, according to the exemplary embodiment, may register the second medical image, in which an anatomic structure of an organ or a blood vessel structure of an organ does not appear, with the first medical image. The medical image registering apparatus 130 performs registration by using one or more anatomic objects which are adjacent to an organ on the outside, instead of using an anatomic structure which directly relates to a disease and an organ of a region of interest that is not identifiable due to noise in the second medical image.

For example, in the case of an ultrasound medical image of a liver cancer patient, information which relates to the disease and the shape of a liver may not be identifiable, but a diaphragm which is adjacent to the interface of the liver and an inferior vena cava (IVC) which is adjacent to the liver are clearly identifiable in the ultrasound image of the liver cancer patient.

The medical image registering apparatus 130 registers the first medical image and the second medical image of the liver region by using information which relates to the diaphragm and the IVC, which appear clearly in both the first medical image and the second medical image. Therefore, even when all information relating to a liver that is an interested organ is lost in the second medical image, the first medical image and the second medical image of the liver region may be registered by using the IVC and the diaphragm.

However, the above-described liver, diaphragm, and IVC are merely exemplary, and exemplary embodiments are not limited thereto. For example, when the organ of interest is a liver, at least one of a portal vein, hepatic vein, and an inferior vena cava (IVC), which are adjacent to the liver, may be used. When the organ of interest is a kidney, at least one of an IVC, a liver, a gallbladder, spleen, and a renal vein, which are adjacent to the kidney, may be used. When the organ of interest is a thyroid gland, at least one of a carotid artery and a jugular vein, which are adjacent to the thyroid gland, may be used. When the organ of interest is a pancreas, at least one of an IVC, a splenic vein, a splenic artery, and spleen, which are adjacent to the pancreas, may be used.

In an exemplary embodiment, the registered image may be a fusion image of the first medical image and the second medical image. In another exemplary embodiment, the registered image may be an image that is obtained by aligning the first medical image and the second medical image at an observation time point. The registered image is displayed on the image display device 140.

Figure 2:
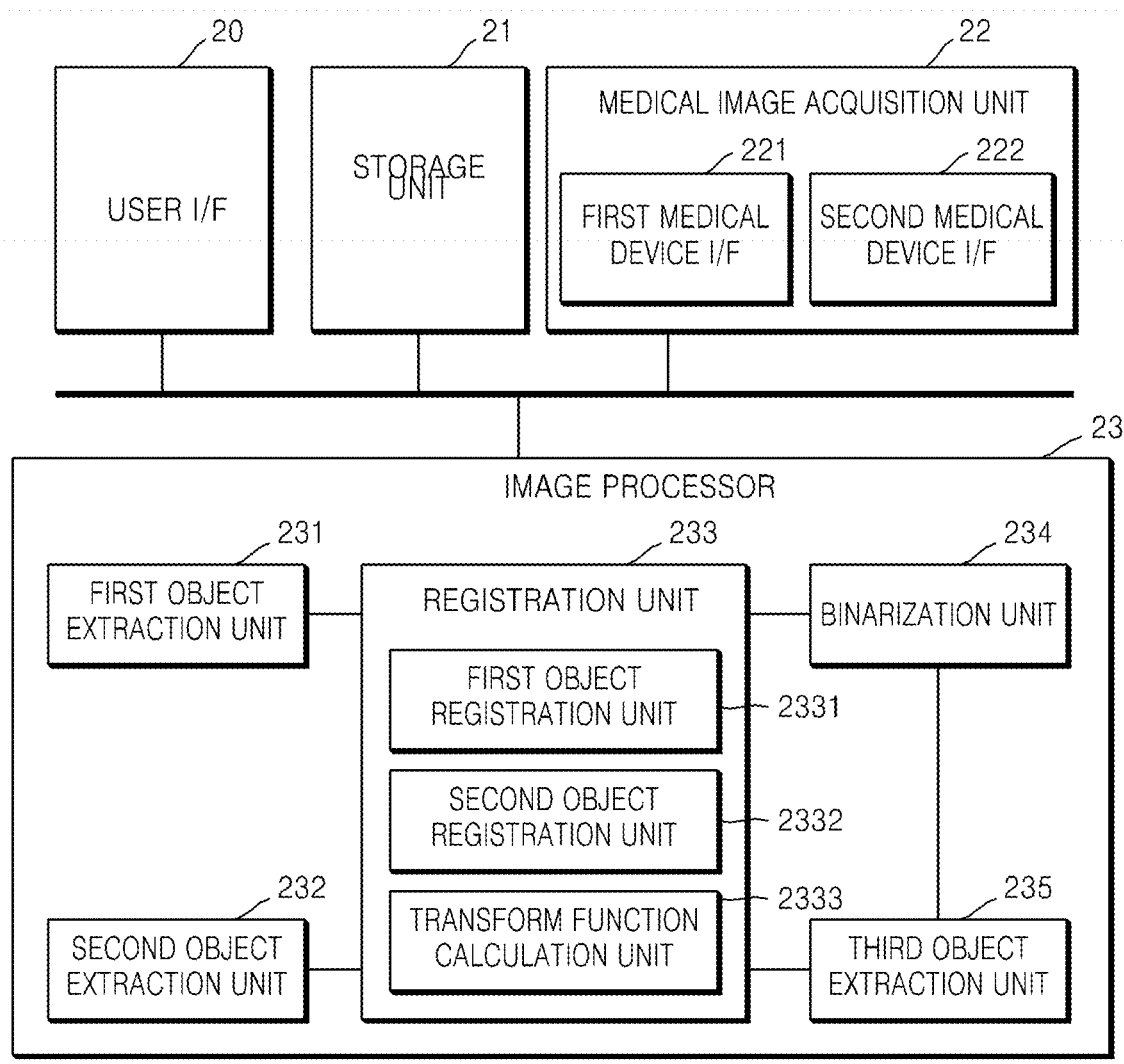
FIG. 2 is a block diagram which illustrates a medical image registering apparatus, according to an exemplary embodiment.

FIG. 2 is a block diagram which illustrates the medical image registering apparatus 130, according to an exemplary embodiment. Referring to FIG. 2, the medical image registering apparatus 130 includes a user interface (I/F) 20, a storage unit (also referred to herein as a "storage" and/or as a "storage device") 21, a medical image acquisition unit (also referred to herein as a "medical image acquisition device") 22, and an image processor 23. However, the medical image registering apparatus 130 may further include general-purpose components other than the illustrated components.

The medical image acquisition unit 22 acquires the first medical image and the second medical image from the first medical device 110 and the second medical device 120. The medical image acquisition unit 22 includes a first medical device interface 221 and a second medical device interface 222 which are respectively configured for acquiring the first medical image and the second medical image from the first medical device 110 and the second medical device 120. The first medical device interface 221 and the second medical device interface 222 are directly or indirectly connected to the first medical device 110 and the second medical device 120.

The first medical device interface 221 may be directly connected to the first medical device 110 in order to acquire the first medical image that is captured in advance of a medical operation to be performed by using the first medical device 110. In another exemplary embodiment, when the first medical image is acquired via an external storage medium (e.g., USB, CD, or DVD) or a network interface, the first medical device interface 221 may be omitted. The medical image acquisition unit 22 stores the acquired first medical image in the storage unit 21. The second medical device interface 222 acquires the second medical image captured by the second medical device 120.

The user interface 20 receives an input from a user for operating the medical image registering apparatus 130, and outputs the registered medical image, the first medical image and the second medical image acquired by the medical image registering apparatus 130. The user interface 20 may include any one or more of a button, a keypad, a switch, a dial, or a touch interface, which enable the user to operate the medical image registering apparatus 130. The user interface 20 may include a touchscreen for displaying an image. In another exemplary embodiment, the user interface 20 may include an input/output (I/O) port for connecting human interface devices (HIDs). The user interface 20 may include an I/O port for inputting/outputting an image.

The user interface 20 may output a 2D section in the first medical image stored in the storage unit 21. Thereafter, the user interface 20 may receive a selection of at least one point in the output section.

The image processor 23 registers the first medical image and the second medical image and outputs the registered medical image to the user interface 20. The first medical image may be loaded from the storage unit 21, and the second medical image may be acquired in real time via the second medical device interface 222.

The image processor 23 extracts, from the first medical image, a first anatomic object which includes the point selected via the user interface 20. The image processor 23 extracts a second anatomic object which is adjacent to the point selected via the user interface 20, from the first medical image. The image processor 23 extracts a third anatomic object which corresponds to the first anatomic object and a fourth anatomic object which corresponds to the second anatomic object, from the second medical image.

The image processor 23 registers the first medical image and the second medical image based on a geometric relation between the anatomic objects extracted from the first medical image and the second medical image (i.e., the first, second, third, and fourth anatomic objects). Herein, the geometric relation may include a vector which corresponds to a relative positional relationship between the anatomic objects.

Based on a result of an operation of registering the first medical image and the second medical image, the image processor 23 calculates a coordinate transform function for transforming or inverse-transforming the coordinates of the second medical image into the coordinates of the first medical image. After the calculation of the coordinate transform function, when the coordinates of the second medical image are changed by the movement/rotation of the probe 121, the image processor 23 uses the coordinate transform function to output the first medical image in correspondence with the changed coordinates of the second medical image. The image processor 23 may use the coordinate transform function to synchronize the view and the coordinates of the first medical image and the second medical image.

The image processor 23 includes a first object extraction unit (also referred to herein as a "first object extractor" and/or as a "first object extraction device") 231, a second object extraction unit (also referred to herein as a "second object extractor" and/or as a "second object extraction device") 232, a registration unit (also referred to herein as a "registerer" and/or as a "registration device") 233, a binarization unit (also referred to herein as a "binarizer" and/or as a "binarization device") 234, and a third object extraction unit (also referred to herein as a "third object extractor" and/or as a "third object extraction device") 235. In the present exemplary embodiment, the image processor 23 extracts two anatomic objects from the first medical image and extracts two anatomic objects from the second medical image; however, exemplary embodiments are not limited thereto. For example, the image processor 23 may extract three or more anatomic objects from either or both medical images in order to increase the accuracy of image registering.

The first object extraction unit 231 extracts the first anatomic object from the first medical image, and the second object extraction unit 223 extracts the second anatomic object from the first medical image.

The first object extraction unit 231 extracts the first anatomic object by using the anatomic feature of the point selected via the user interface 20. In order to determine a region of the first anatomic object, the first object extraction unit 231 detects points that are adjacent to the selected point and have an anatomic feature which is similar to the anatomic feature of the selected point.

The first object extraction unit 231 determines the region of the first anatomic object, which region includes the selected point, by using the detected points. For example, in order to detect points which have an anatomic feature which is similar to the anatomic feature of the selected point, the first object extraction unit 231 may detect points, a brightness value difference (that is, a contrast) of which, with respect to the selected point, is smaller than or equal to a critical value, in the first medical image that is contrast-enhanced. In this case, the first object extraction unit 231 may extract points, a brightness value difference of each of which, with respect to the selected point, is smaller than or equal to a critical value, and which are located within a predetermined distance from the selected point, and extract points, a brightness value difference of which, with respect to the extracted points, is smaller than or equal to a critical value, and which are located within a predetermined distance from the extracted points. This will be described below in detail with reference to FIG. 4.

The second object extraction unit 232 may detect points which have brightness values which fall within a predetermined brightness value range (Imin, Imax) in the first medical image that is contrast-enhanced. The second object extraction unit 232 may calculate a probability that the detected points will be included in the region of the second anatomic object, and form one or more clusters which are constructed by points for which the calculated probability is greater than or equal to a predetermined critical value. The second object extraction unit 232 may extract a cluster which has a maximum volume from among the one or more formed clusters, as the second anatomic object.

The brightness value of the selected point which is selected in order to extract the first anatomic object from the first medical image may not fall within the predetermined brightness value range (Imin, Imax), in order to extract the second anatomic object from the first medical image.

The binarization unit 234 generates a binarized image of the second medical image based on the brightness value of the second medical image. The binarization unit 234 may determine a critical brightness value based on the ultrasound reflection characteristics of the fourth anatomic object to be extracted from the second medical image. In this case, the fourth anatomic object may correspond to the second anatomic object of the first medical image.

The binarization unit 234 may binarize the second medical image by using the determined critical brightness value. The binarization unit 234 may represent candidate points, which are candidates for the fourth anatomic object, by using a '1', and may represent the other points by using a '0'. As described above, in the B-mode ultrasound image, the diaphragm has ultrasound reflection characteristics of a relatively large brightness value, and the IVC has ultrasound reflection characteristics of a relatively small brightness value. Therefore, in a case of diaphragm extraction, candidate points are points which have a value of '1' in the binarized image.

The third object extraction unit 235 extracts the third anatomic object and the fourth anatomic object from the second medical image.

The first anatomic object corresponds to the third anatomic object, and the second anatomic object corresponds to the fourth anatomic object. Herein, the anatomic objects which respectively correspond to each other may be the same anatomic objects, or may be adjacent anatomic objects. For example, the first anatomic object may be an IVC in the MR image, the second anatomic object may be a liver in the MR image, the third anatomic object may be an IVC in the ultrasound (US) image, and the fourth anatomic object may be a diaphragm in the US image. In this case, the liver and the diaphragm are not the same anatomic objects, but are anatomic objects which correspond to each other, because the interface of the liver contacts the diaphragm. In particular, when the diaphragm is considered as the interface of the liver, the position of the liver may be detected by using the position of the diaphragm.

For example, the third object extraction unit 235 calculates eigenvalues of a Hessian matrix of the second medical image at the respective candidate points of the binarized image binarized by the binarization unit 234. Based on the calculated eigenvalues, the third object extraction unit 235 determines whether the respective candidate points of the second medical image are included in the fourth anatomic object to be extracted from the second medical image. In order to determine whether the respective candidate points of the binarized image are included in the fourth anatomic object to be extracted from the second medical image, the third object extraction unit 235 may calculate a flatness based on the calculated eigenvalues, and then determine, based on the calculated flatness, whether each of the respective candidate points is included in the fourth anatomic object. Based on the determination result, the third object extraction unit 235 extracts the fourth anatomic object from the second medical image.

The third object extraction unit 235 may extract a boundary of the fourth anatomic object and then perform curve fitting on the extracted boundary in order to extract a curve which corresponds to the boundary.

Further, the third object extraction unit 235 may determine points which are included in a region which is located within a predetermined distance from the extracted boundary as candidate points, and calculate eigenvalues of a Hessian matrix with respect to the respective candidate points.

Based on the calculated eigenvalues, the third object extraction unit 235 determines whether the respective candidate points are included in the third anatomic object. In order to determine whether the respective candidate points are included in the third anatomic object to be extracted from the second medical image, the third object extraction unit 235 may calculate a vesselness based on the calculated eigenvalues, and then determine, based on the calculated vesselness, whether the respective candidate points are included in the fourth anatomic object. Based on the determination result, the third object extraction unit 235 extracts the third anatomic object from the second medical image.

The registration unit 233 registers the first medical image and the second medical image. The registration unit 233 registers the first medical image and the second medical image by comparing an anatomic relation between the first anatomic object and the second anatomic object and an anatomic relation between the third anatomic object and the fourth anatomic object. The registration unit 23 includes a first object registration unit (also referred to herein as a "first object registerer" and/or as a "first object registration device") 2331, a second object registration unit (also referred to herein as "second object registerer" and/or as a "second object registration device") 2332, and a transform function calculation unit (also referred to herein as a "transform function calculator" and/or as a "transform function calculation device") 2333.

The first object registration unit 2331 aligns the first medical image and the second medical image by using the first anatomic object extracted from the first medical image. For example, the first object registration unit 2331 aligns the first medical image such that the first anatomic object of the first medical image is disposed in a predetermined coordinate axis direction. The first object registration unit 2331 aligns the second medical image such that the third anatomic object is disposed in the disposition direction of the first anatomic object.

While the first medical image and the second medical image are aligned, the second object registration unit 2332 shifts and/or rotates the first medical image or the second medical image by using the second anatomic object. For example, the second object registration unit 2332 rotates and/or shifts the first medical image or the second medical image such that a distance difference between the second anatomic object and the third anatomic object is minimized. In this case, the second object registration unit 2332 rotates and/or shifts the first medical image or the second medical image within a range that the first anatomic object and the third anatomic object are not misaligned.

Due to use of the first object registration unit 2331 and the second object registration unit 2332, the geometric relation between the first anatomic object and the second anatomic object of the first medical image becomes identical to the geometric relation between the third anatomic object and the fourth anatomic object of the second medical image.

The transform function calculation unit 2333 maps the coordinate systems of the first medical image and the second medical image that have been aligned, shifted, and/or rotated by the first object registration unit 2331 and the second object registration unit 2332. For example, the transform function calculation unit 2333 calculates a transform function for transforming the coordinates of the original second medical image before the processing of the first object registration unit 2331 and the second object registration unit 2332 into the coordinates of the second medical image after the processing of the first object registration unit 2331 and the second object registration unit 2332.

A more detailed operation of the medical image registering apparatus 130 will be described with reference to a medical image registering method that will be described below. In the following description, those of ordinary skill in the art will understand which component of the medical image registering apparatus 130 performs the corresponding process based on the description above.

Figure 3:
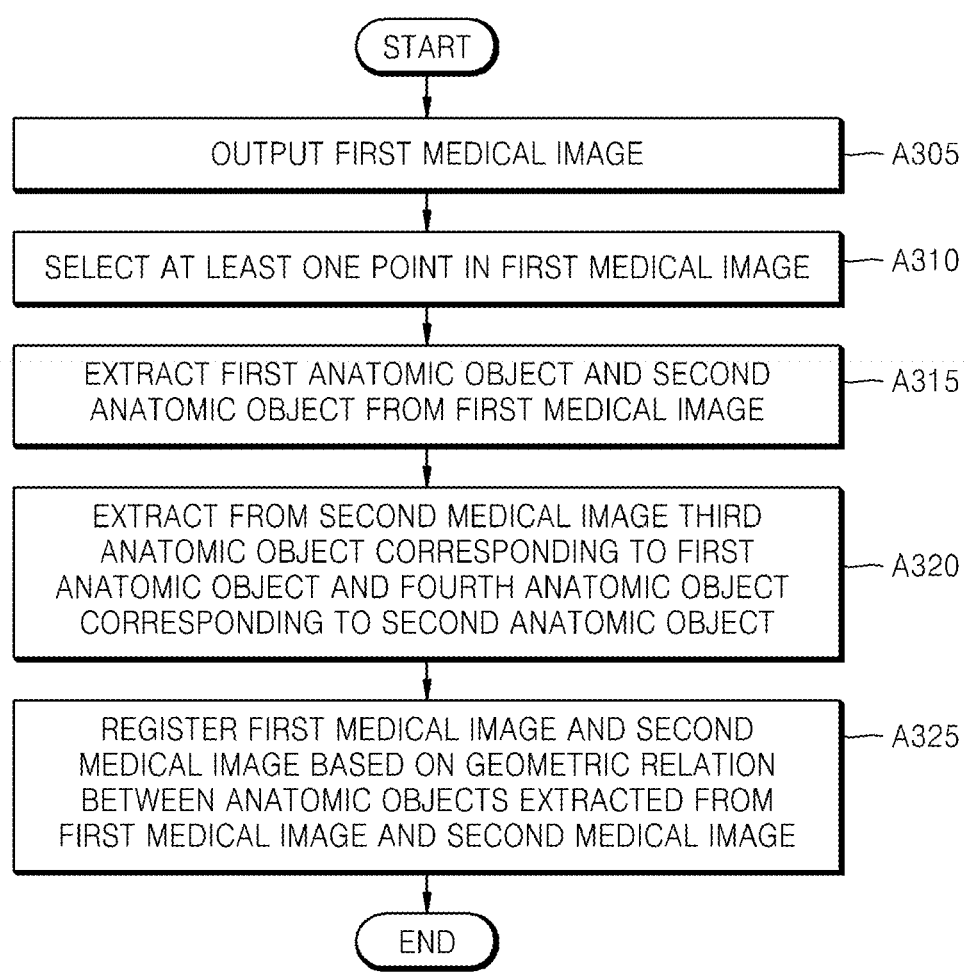
FIG. 3 is a flowchart which illustrates a medical image registering method, according to an exemplary embodiment.

FIG. 3 is a flowchart which illustrates a medical image registering method, according to an exemplary embodiment.

Figure 9:
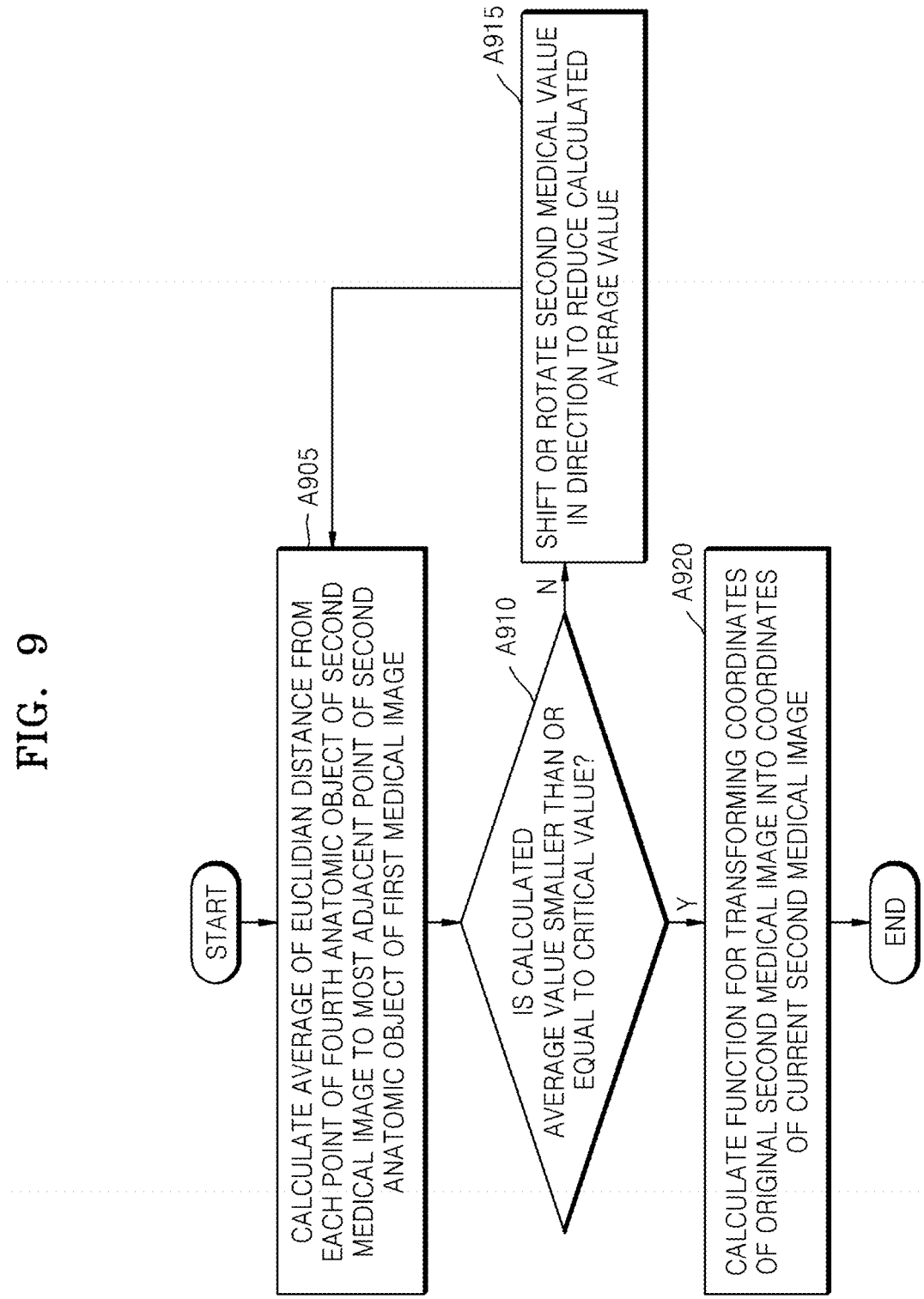
FIG. 9 is a flowchart which illustrates a method for calculating a coordinate transform function, according to an exemplary embodiment.

Referring to FIG. 3, in operation A305, the medical image registering apparatus 130 outputs the first medical image. For example, the medical image registering apparatus 130 outputs a 3D section of the first medical image stored. In this case, the medical image registering apparatus 130 may receive an input from the user which relates to which section is to be output. An image G91 of FIG. 9 is an MR image of any one section of a liver region which is output by the medical image registering apparatus 130.

Figure 10:
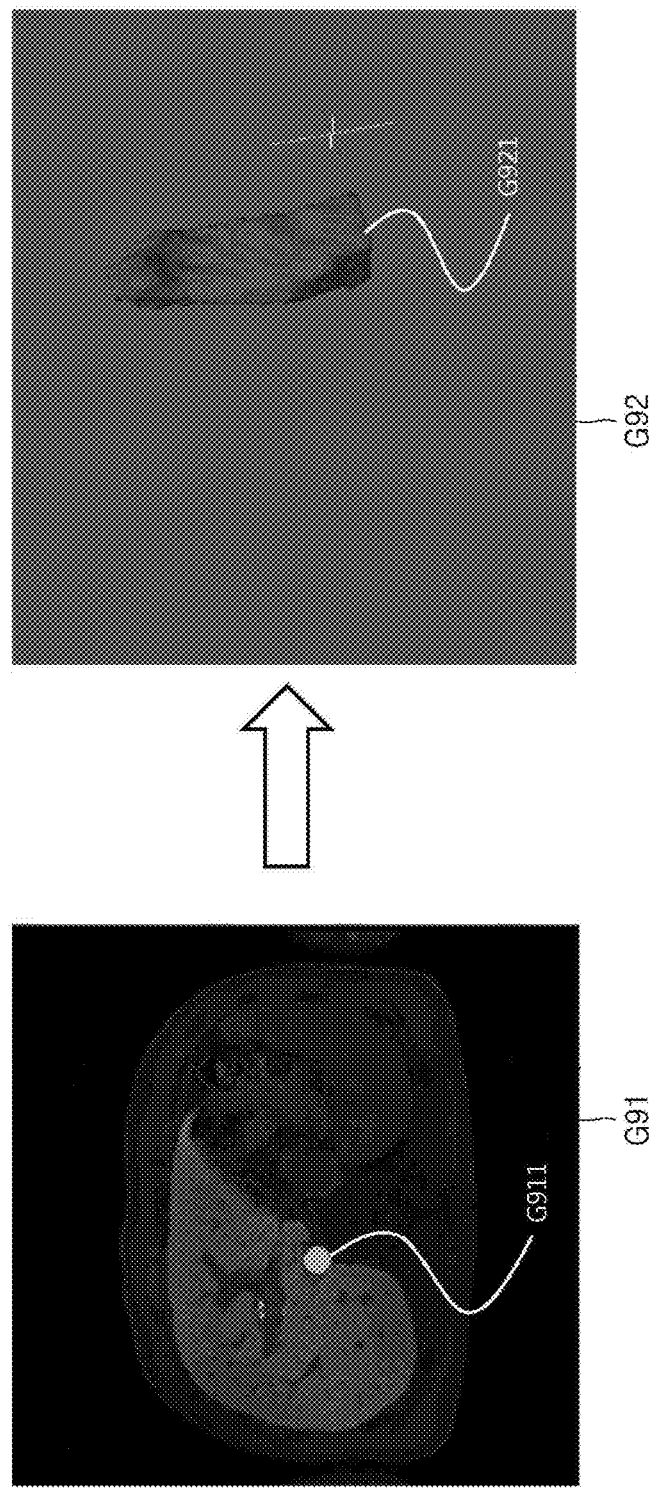
FIGS. 10, 11A, 11B, 11C, 12, 13, 14A, 14B, 15A, 15B, 15C, and 16 are diagrams which illustrate medical images which are usable in conjunction with the medical image registering method, according to exemplary embodiments.

In operation A310, the medical image registering apparatus 130 receives a selection of at least one point in the first medical image. For example, the medical image registering apparatus 130 may receive a user's selection of a point G911 in the image G91 of FIG. 10. For example, the user may select the point G911 as representing the anatomic feature of an IVC in the MR image G91 that is contrast-enhanced. As another example, the medical image registering apparatus 130 may automatically extract the point G911 as representing the anatomic feature of the IVC, based on the brightness value of the points included in the first medical image.

In operation A315, the medical image registering apparatus 130 extracts the first anatomic object and the second anatomic object from the first medical image. An exemplary embodiment of a process for extracting the first anatomic object by the medical image registering apparatus 130 will be described with reference to FIG. 4.

Figure 4:
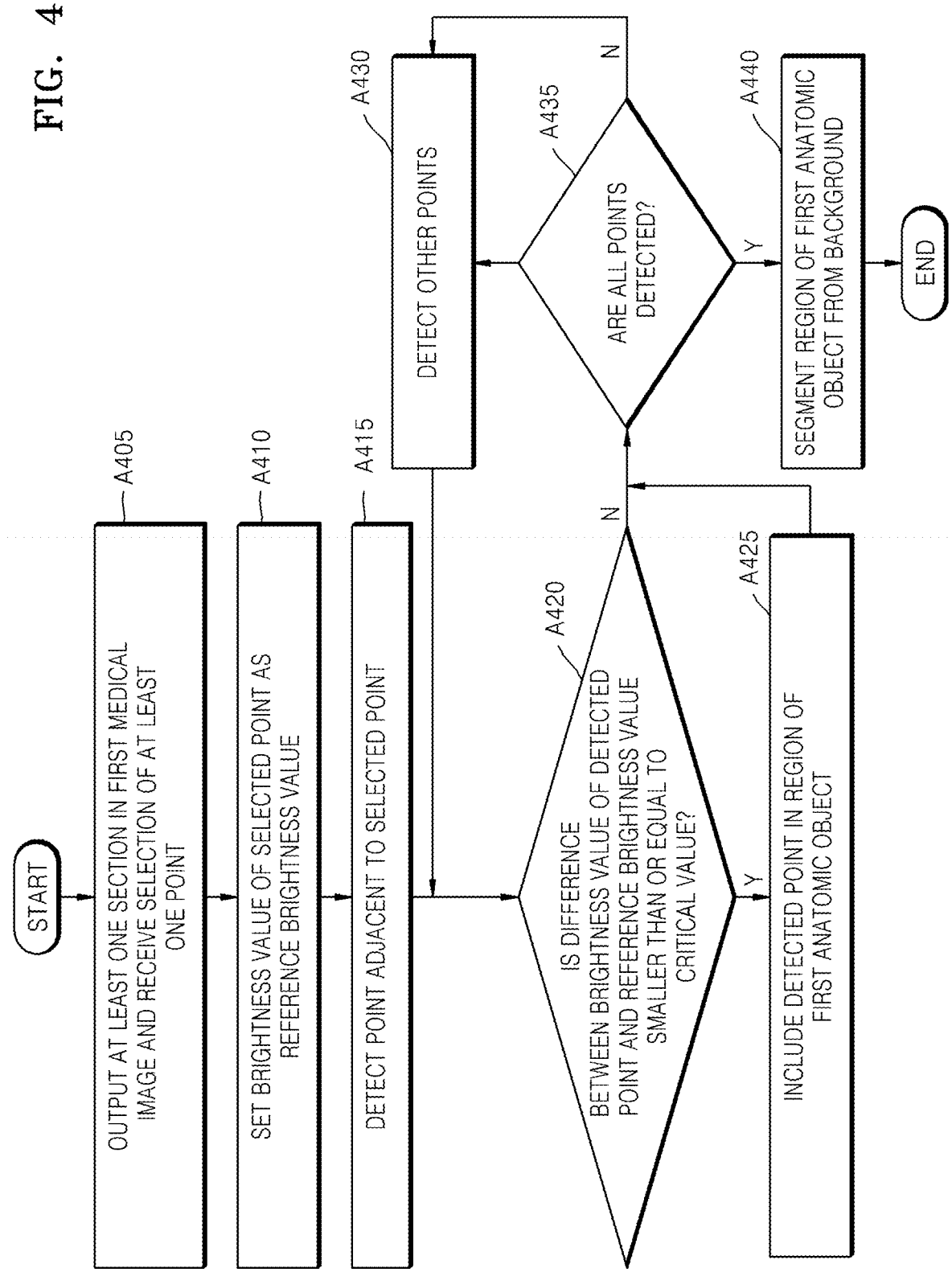
FIG. 4 is a flowchart which illustrates a method for extracting an anatomic object, according to an exemplary embodiment.

Referring to FIG. 4, in operation A405, the medical image registering apparatus 130 outputs any one section in the first medical image and receives a selection of at least one point in the first medical image. This corresponds to operations A305 and A310 of FIG. 3, and thus a redundant description thereof will be omitted.

In operation A410 medical image registering apparatus 130 sets a brightness value of the selected point as a reference brightness value. For example, the medical image registering apparatus 130 sets a brightness value of the point G911 as the reference brightness value. The reference brightness value is used to determine whether a point in the first medical image is included in the first anatomic object.

In operation A415, the medical image registering apparatus 130 detects a point which is adjacent to the selected point in the first medical image. The point adjacent to the selected point may be a point which contacts the selected point, but is not limited thereto. The medical image registering apparatus 130 may detect a point which is located within a predetermined distance from the selected point, as the point adjacent to the selected point.

For example, information which relates to a shape and/or a size of the first anatomic object, among the features of the first anatomic object, may be input in advance in the medical image registering apparatus 130. When information relating to the diameter of an IVC is input in advance in the medical image registering apparatus 130, the medical image registering apparatus 130 may detect the point which is adjacent to the selected point, as being a point which is located within the range of the diameter of the IVC from the selected point.

The point which is adjacent to the selected point may be located at the section corresponding to the selected point, or may be located at a section which is adjacent to the section which includes the selected point. For example, the point adjacent to the selected point may be detected in the image G91, or may be detected in the sections (not illustrated) adjacent to the image G91. In particular, the medical image registering apparatus 130 may detect the point adjacent to the selected point in a 3D space of the first medical image, based on the selected point.

In operation A420, the medical image registering apparatus 130 compares the brightness value of the detected point with the reference brightness value. For example, the medical image registering apparatus 130 calculates a difference between the brightness value of the selected point G911 and the brightness value of the detected point. The medical image registering apparatus 130 determines whether a difference between the brightness value of the detected point and the reference brightness value is smaller than or equal to a critical value. The critical value may be preset in the medical image registering apparatus 130.

When the difference between the brightness value of the detected point and the reference brightness value is smaller than or equal to the critical value, in operation A425, the medical image registering apparatus 130 includes the detected point in a region of the first anatomic object. This may be understood as a growing region that expands the region of the first anatomic object by using the selected point as a seed value of the first anatomic object. When the difference between the brightness value of the detected point and the reference brightness value is greater than the critical value, the medical image registering apparatus 130 determines that the detected point is not included in the region of the first anatomic object.

In operation A435, the medical image registering apparatus 130 determines whether all points have been detected in the first medical image. The medical image registering apparatus 130 may determine whether all points have been detected in the first medical image, based on the feature of the first anatomic object that is input in advance. For example, the medical image registering apparatus 130 determines whether all points have been detected within the range of the diameter of the IVC from the point G911 selected in the image G911. The medical image registering apparatus 130 may detect other sections in a similar way to the image G91, and the range of the other sections to be detected may be determined in consideration of the length of the IVC in the liver region. In particular, the number of detected sections decreases as the length of the IVC decreases. Further, the number of detected sections increases as the length of the IVC increases.

When all points have not been detected in the first medical image, in operation A430, the medical image registering apparatus 130 detects undetected other points. The method of detecting other points is similar to the method of selecting the adjacent point in operation A415. In operation A430, the medical image registering apparatus 130 may preferentially detect a point which is adjacent to the last point included in the first anatomic object in operation A425. According to an exemplary embodiment, the reference brightness value may be adjusted in operation A430. For example, the reference brightness value may be adjusted based on the brightness value of the last point included in the first anatomic object in operation A425; however, exemplary embodiments are not limited thereto.

When all points have been detected in the first medical image, in operation A440, the medical image registering apparatus 130 segments the region of the first anatomic object from the background. For example, a 3D IVC G921 segmented from the background is illustrated in the image G92 of FIG. 10.

Figure 5:
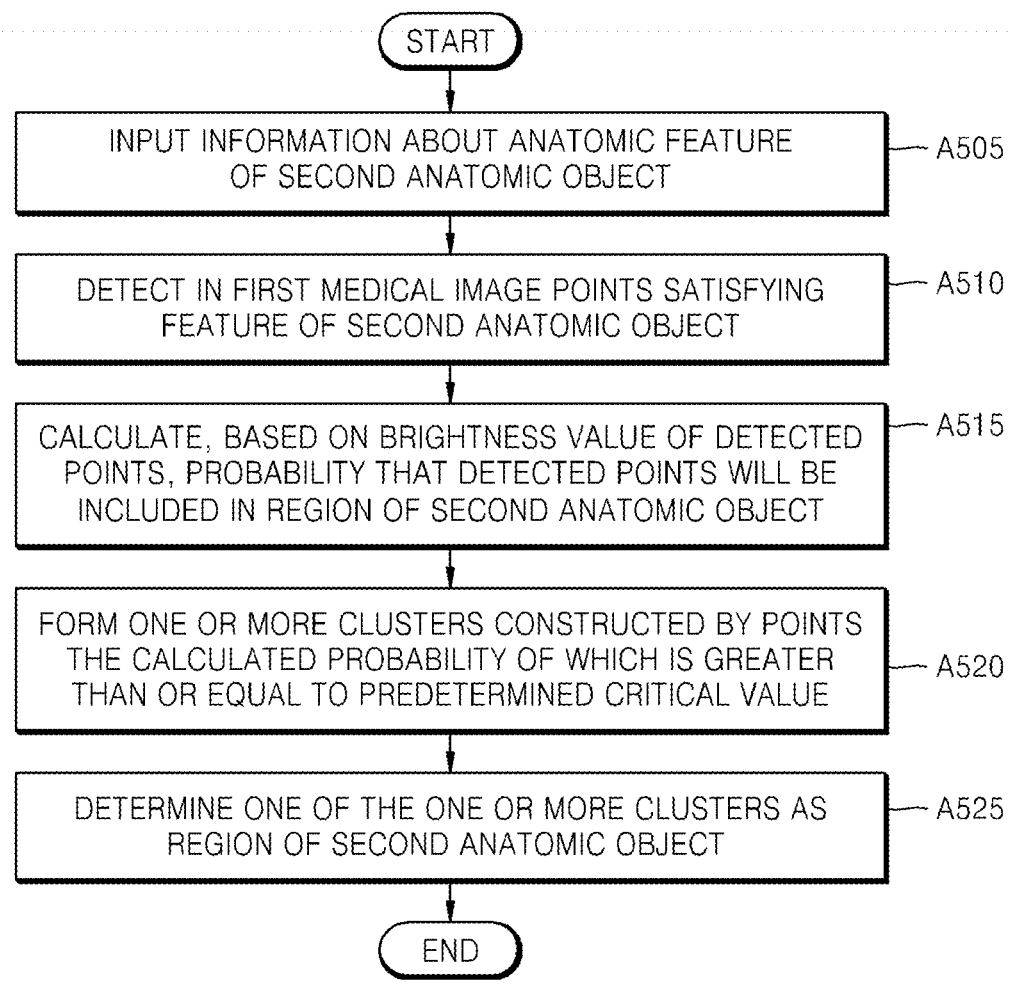
FIG. 5 is a flowchart which illustrates a method for extracting an anatomic object, according to an exemplary embodiment.

An exemplary embodiment of a process for extracting the second anatomic object from the first medical image by the medical image registering apparatus 130 will be described with reference to FIG. 5.

In operation A505, the medical image registering apparatus 130 receives an input of information which relates to the anatomic feature of the second anatomic object. For example, information relating to the features of various anatomic objects may be input in advance in the medical image registering apparatus 130. When the first medical image is an image of the liver region, the medical image registering apparatus 130 may be set in advance to select the IVC as the first anatomic object and to select the liver as the second anatomic object. When the liver is selected as the second anatomic object, the medical image registering apparatus 130 loads information which relates to the anatomic feature of the second anatomic object. For example, the information relating to the second anatomic object may include information relating to the brightness value range, shape and/or volume of the second anatomic object.

In operation A510, the medical image registering apparatus 130 detects points which satisfy the criteria which relate to the feature of the second anatomic object, in the first medical image. For example, the medical image registering apparatus 130 detects points within the (minimum brightness value Imin, maximum brightness value Imax) range of the second anatomic object. The medical image registering apparatus 130 may perform detection with respect to a plurality of sections. For example, the number of sections to be detected may be determined based on information which relates to a shape and a volume of the second anatomic object.

Based on the brightness value of the detected points within the (minimum brightness value Imin, maximum brightness value Imax) range, in operation A515, the medical image registering apparatus 130 may calculate a probability that the detected points are included in the region of the second anatomic object.

The probability that the detected points (first point) are included in the region of the second anatomic object may be expressed as Equation 1 according to Bayes Rule.

$$p(x|z) = p(z|x)\frac{1}{p(z)}p(x) \quad \text{[Equation 1]}$$
$$\approx p(z|x)p(x)$$

In Equation 1, p(z|x) denotes a likelihood function of a brightness value z of the first point. The likelihood function of the brightness value z of the first point may represent the probability of being the brightness value z of the first point when a brightness value x of a point which is included in the region of the second anatomic object is given.

Further, p(x) is a probability function which represents a connectivity at the first point, and may be calculated by applying Equation 2 as expressed below.

$$p(x) = e^{-E(x)}, E(x) = \sum_{\langle j \in N(i)\rangle} |z_i - z_j| \quad \text{[Equation 2]}$$

In Equation 2, $z_i$ denotes a brightness value of an $i^{th}$ point (first point), and $z_j$ denotes a brightness value of a $j^{th}$ point included in points N(i) around the $i^{th}$ point (first point).

A method of acquiring p(z|x) will be described below in detail with reference to FIGS. 11A, 11B, and 11C.

Figure 11:
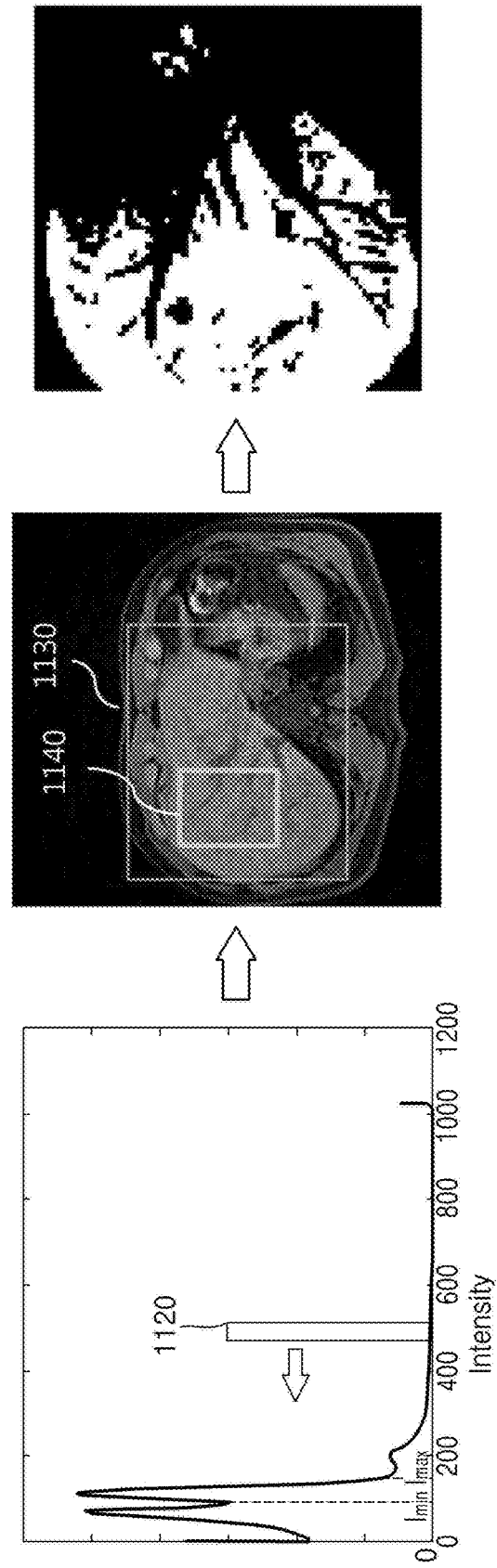

Referring to FIG. 11A, the medical image registering apparatus 130 may acquire a histogram of points (i.e., first points) within the (minimum brightness value Imin, maximum brightness value Imax) range in the first medical image. For example, an x axis of the histogram may represent a brightness value, and a y axis may represent the number of points (voxels) which have the brightness value.

Further, as illustrated in FIG. 11B, the medical image registering apparatus 130 may acquire a region which corresponds to the first points as a candidate region 1130 of the second anatomic object.

In addition, the medical image registering apparatus 130 may extract a brightness value range having a maximum volume in a window of a predetermined size. The medical image registering apparatus 130 may acquire a region which corresponds to the points (i.e., second points) included in the extracted brightness value range as a sample region 1130 of the second anatomic object.

The medical image registering apparatus 130 may calculate an average value and a standard deviation of the points (i.e., second points) included in the sample region 1130 of the second anatomic object, and acquire a normal distribution having the calculated average value and standard deviation.

The medical image registering apparatus 130 may calculate a likelihood function p(z|x) for the brightness value z of the first point based on the acquired normal distribution and the brightness value of the first points.

In operation A520, the medical image registering apparatus 130 may form one or more clusters (i.e., candidate clusters) including points at which the probability calculated by applying Equation 2 is greater than or equal to a critical value.

In operation A525, the medical image registering apparatus 130 may determine one of the formed one or more clusters as corresponding to the region of the second anatomic object.

In this case, the medical image registering apparatus 130 may determine the cluster which has the maximum volume from among the one or more formed candidate clusters as corresponding to the region of the second anatomic object. As another example, the medical image registering apparatus 130 may determine the cluster which is most adjacent to the volume of the second anatomic object that is input in advance as corresponding to the region of the second anatomic object.

As another example, the medical image registering apparatus 130 may calculate a respective probability that each cluster will be included in the region of the second anatomic object, and determine the cluster having the greatest probability as corresponding to the region of the second anatomic object.

The probability that the cluster will be included in the region of the second anatomic object may be an average value of the respective probabilities that each of the points included in the cluster will be included in the region of the second anatomic object.

Figure 12:
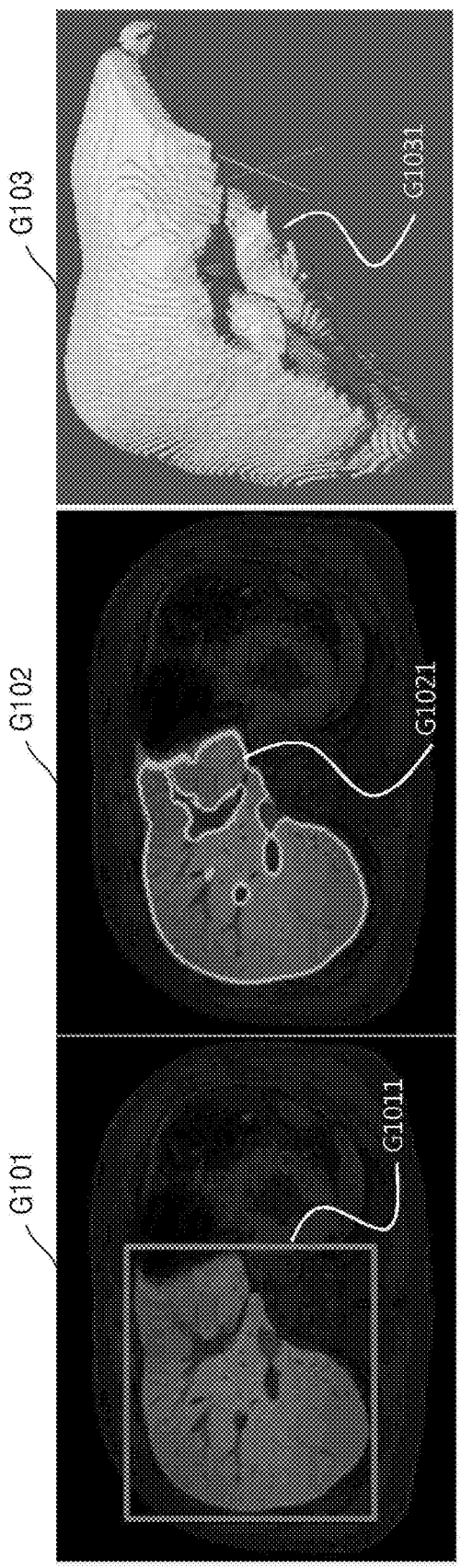

The medical image registering apparatus 130 may segment the region of the second anatomic object from the background. In FIG. 12, an image G101 is a 2D section of the first medical image, and a box G1011 represents a liver to be extracted. An image G102 represents a region G1021 of the liver in any one section of the first medical image as a result of operation A525. An image G103 represents a liver G1031 segmented from the first medical image.

Referring to FIG. 3, in operation A320, the medical image registering apparatus 130 extracts a third anatomic object which corresponds to the first anatomic object and a fourth anatomic object which correspond to the second anatomic object, from the second medical image. For example, the medical image registering apparatus 130 may extract an IVC and a diaphragm from the second medical image.

An exemplary embodiment of a process for extracting the fourth anatomic object (e.g., diaphragm) from the second medical image by the medical image registering apparatus 130 will be described with reference to FIG. 6.

Figure 6:
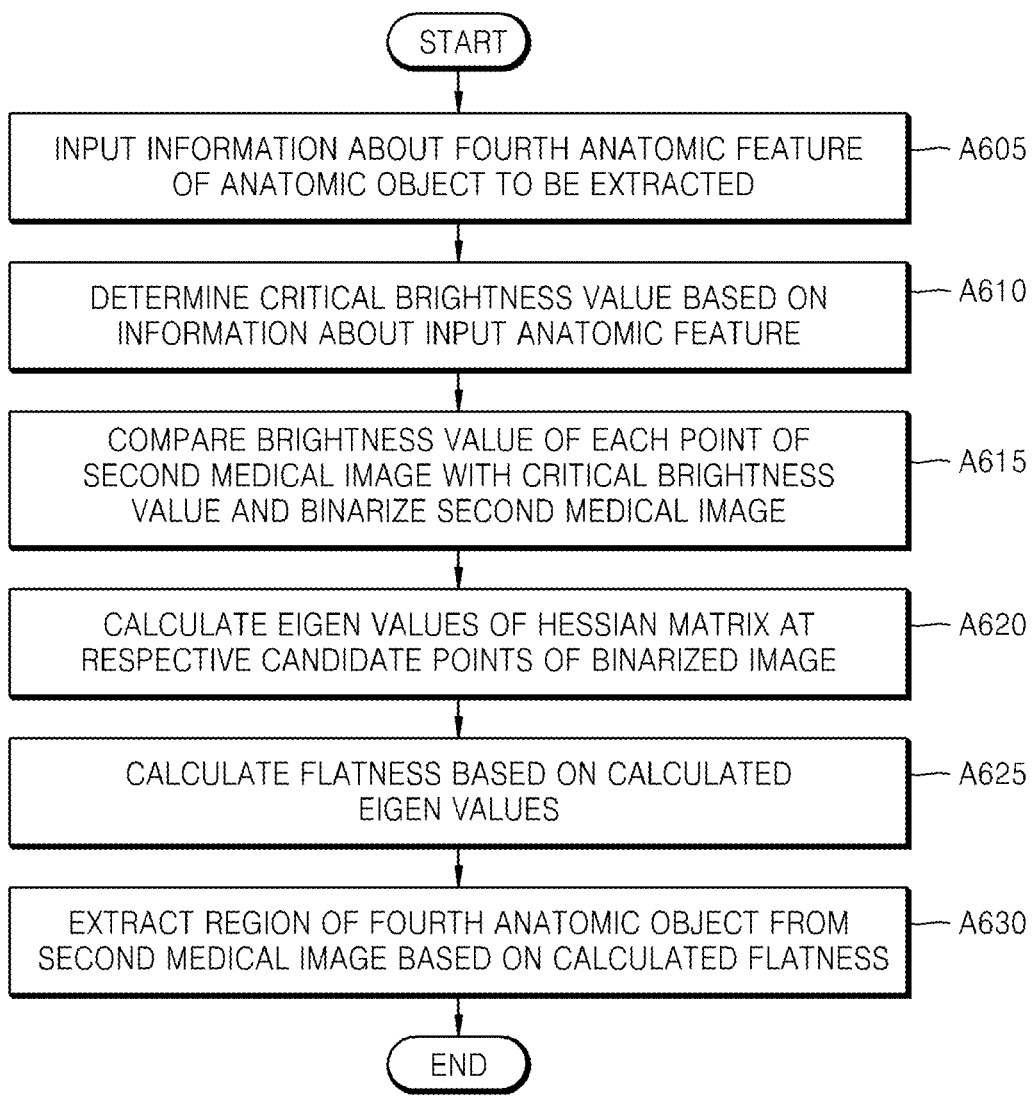
FIG. 6 is a flowchart which illustrates a method for extracting an anatomic object, according to an exemplary embodiment.

Referring to FIG. 6, in operation A605, the medical image registering apparatus 130 receives an input of information which relates to an anatomic feature of the fourth anatomic object to be extracted. For example, information relating to the feature of the fourth anatomic object may be input in advance in the medical image registering apparatus 130 before extraction of the fourth anatomic object.

For example, when the user requests the medical image registering apparatus 130 to register medical images of the liver region, the medical image registering apparatus 130 loads information which relates to the features of the IVC and the diaphragm in order to extract the IVC and the diaphragm from the ultrasound image. However, because the IVC and the diaphragm are sequentially extracted from the second medical image, the medical image registering apparatus 130 loads information relating to the anatomic object to be extracted first among the IVC and the diaphragm.

In operation A610, the medical image registering apparatus 130 determines a critical brightness value, which is used to extract the fourth anatomic object, based on the information relating to the anatomic feature that is input. The critical brightness value is a reference brightness value for binarizing the second medical image, and is determined based on the ultrasound reflection characteristics of the anatomic object to be extracted. For example, in FIG. 13, an image G111 represents a 2D section of the second medical image. Item G1111, which is represented to be brighter than the background, represents the diaphragm, and item G1112, which is represented to be darker than the background, represents the IVC.

A critical brightness value T(x, y, z) at a point (x, y, z) of the second medical image may be determined via Equation 3.

$$T(x,y,z)=m(x,y,z)+\lambda \cdot \delta(x,y,z) \quad \text{[Equation 3]}$$

In Equation 3, m(x, y, z) denotes an average (median) of brightness in a 3D window region with a size of w1×w2×w3 having a center point (x, y, z), δ(x, y, z) denotes a standard deviation in the 3D window region, and λ denotes a weight that is predetermined based on the ultrasound reflection characteristics of the anatomic object to be extracted. For example, λ may be determined within a range of 0 to 1. The size w1×w2×w3 of the window region may also be determined based on the feature of the anatomic object to be extracted. For example, the size w1×w2×w3 of the window region may be determined in consideration of the fact that the diaphragm has a shape of a thin curved surface. The size of the window region increases as the volume of the anatomic object increases.

In operation A615, the medical image registering apparatus 130 binarizes the second medical image by comparing the brightness value of each point of the second medical image with the critical brightness value. For example, when extracting the diaphragm, the medical image registering apparatus 130 generates a binarized image of the second medical image by binarizing the brightness value of voxels not included in the diaphragm into '0' and binarizing the brightness value of the other voxels into '1'. The voxels binarized into '1' represent candidate points of the diaphragm.

A binarization result b(x, y, z) at the point (x, y, z) of the second medical image may be expressed via Equation 4.

$$b(x, y, z) = \begin{cases} 1, & \text{if } I(x, y, z) \geq T(x, y, z) \\ 0, & \text{otherwise} \end{cases} \quad \text{[Equation 4]}$$

In Equation 4, I(x, y, z) denotes a brightness value of the point (x, y, z). Those of ordinary skill in the art will understand that Equation 4 may be modified to extract only a region that is darker than the critical brightness value, according to exemplary embodiments.

In operation A620, the medical image registering apparatus 130 calculates eigenvalues of a Hessian matrix of the second medical image at the respective candidate points of the binarized image. The Hessian matrix is a total differential matrix, and a second-order differential function may be used to determine a region of the image in which a voxel value changes abruptly. Herein, the region in which a voxel value changes abruptly is interpreted as a boundary region of the anatomic object.

$$H_\sigma(x, y, z) = \begin{bmatrix} \frac{\partial^2 I_\sigma}{\partial x \partial x} & \frac{\partial^2 I_\sigma}{\partial x \partial y} & \frac{\partial^2 I_\sigma}{\partial x \partial z} \\ \frac{\partial^2 I_\sigma}{\partial y \partial x} & \frac{\partial^2 I_\sigma}{\partial y \partial y} & \frac{\partial^2 I_\sigma}{\partial y \partial z} \\ \frac{\partial^2 I_\sigma}{\partial z \partial x} & \frac{\partial^2 I_\sigma}{\partial z \partial y} & \frac{\partial^2 I_\sigma}{\partial z \partial z} \end{bmatrix} \quad \text{[Equation 5]}$$

In Equation 5, $H_\sigma(x, y, z)$ denotes a Hessian matrix which relates to a candidate point (x, y, z) of the binarized image, and $I_\sigma$ denotes a brightness value of the candidate point (x, y, z) in the second medical image. The medical image registering apparatus 130 calculates eigenvalues λ1, λ2, λ3 by performing eigenvalue decomposition on the Hessian matrix $H_\sigma$.

In operation A625, the medical image registering apparatus 130 calculates a flatness based on the calculated eigenvalues. For example, when extracting the diaphragm, the medical image registering apparatus 130 performs a flatness test by using Equation 6.

$$\text{Flatness}=T_1 \cdot T_2 \cdot T_3 \quad \text{[Equation 6]}$$

In Equation 6, $$T_1 = e^{(1-|\lambda_1|/|\lambda_3|)^2}, T_2 = e^{(1-|\lambda_2|/|\lambda_3|)^2}, T_3 = (\lambda_1)^2 + (\lambda_2)^2 + (\lambda_3)^2,$$

and the calculated eigenvalues λ1, λ2, and λ3 may satisfy $|\lambda_3| \geq |\lambda_2| \geq |\lambda_1|$.

Based on the calculated flatness, in operation A630, the medical image registering apparatus 130 extracts the region of the fourth anatomic object from the second medical image.

For example, the medical image registering apparatus 130 may determine a candidate point (x, y, z) at which the flatness calculated by Equation 6 is greater than or equal to a predetermined critical value as being a point which is included in a diaphragm (i.e., the fourth anatomic object) region.

An exemplary embodiment of a process for extracting the third anatomic object from the second medical image by the medical image registering apparatus 130 will be described with reference to FIG. 7.

Figure 7:
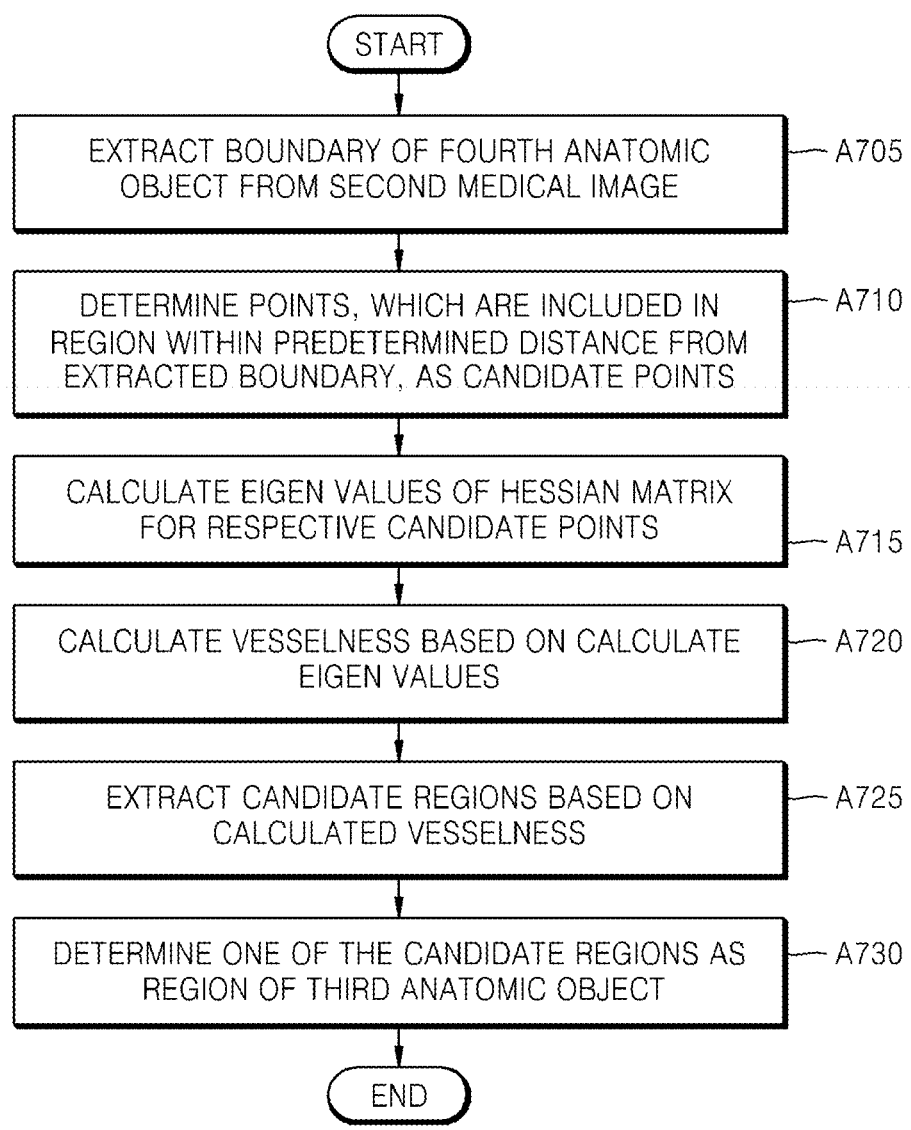
FIG. 7 is a flowchart which illustrates a method for extracting an anatomic object, according to an exemplary embodiment.

Referring to FIG. 7, in operation A705, the medical image registering apparatus 130 may extract a boundary of the fourth anatomic object which is extracted in operation A630 of FIG. 6.

Figure 14A:
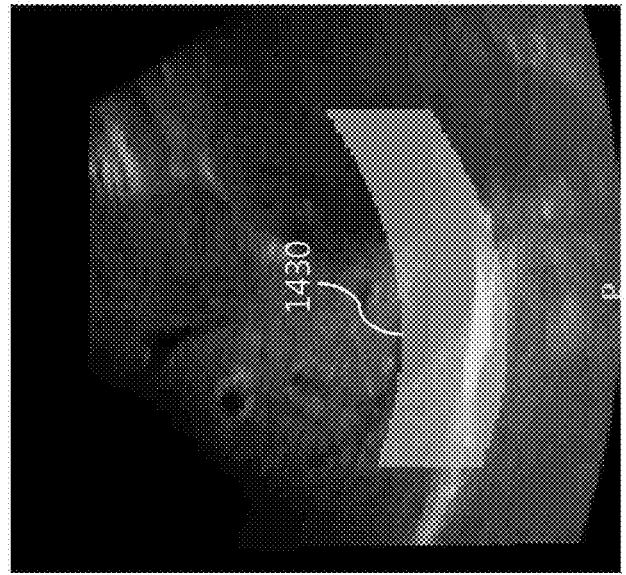

For example, a diaphragm (fourth anatomic object) which is adjacent to the surface to a liver has a curved surface, a boundary 1410 of the diaphragm may be represented as a curve in a two-dimensional (2D) image, as illustrated in FIG. 14A. Accordingly, the medical image registering apparatus 130 may perform curve fitting on a boundary region of the diaphragm in order to extract a curve f(x, z) which corresponds to the boundary.

In operation A710, the medical image registering apparatus 130 may determine points which are included in a region within a predetermined distance from the boundary extracted in operation A705 of FIG. 7 as candidate points. For example, by applying a mask (x, y, z) of Equation 7 below to a point (x, y, z) of the second medical image, voxels having a result value of '1' may be determined as a candidate point of the IVC (third anatomic object).

$$\text{Mask}(x, y, z) = \begin{cases} 1 & f(x, z) \le \text{Mask} \le f(x, z) + t \\ 0 & \text{otherwise} \end{cases} \quad \text{[Equation 7]}$$

In this case, t may be a distance value which is determined in consideration of the diameter of the IVC, and may be, for example, equal to approximately 4.5 cm, but is not limited thereto.

Figure 14B:
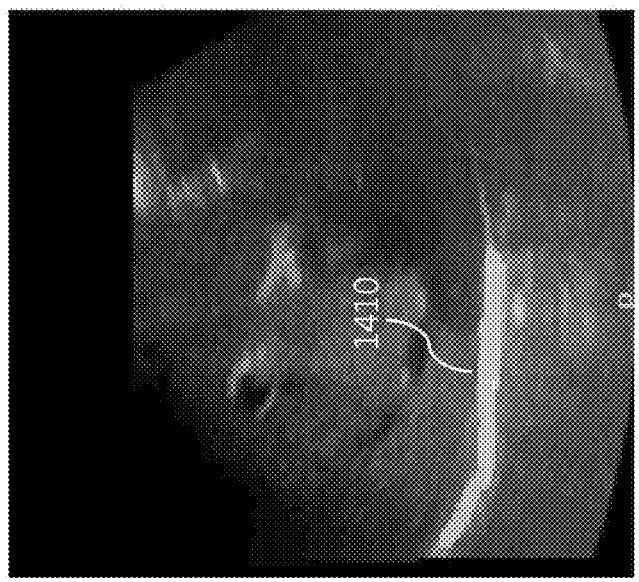

For example, as illustrated in FIG. 14B, voxels included in a region 1430 within a predetermined distance from a curve which corresponds to the boundary of the diaphragm may be a candidate point of the IVC.

In operation A715, the medical image registering apparatus 130 calculates eigenvalues of a Hessian matrix for each candidate point of the image to which the mask has been applied.

Because a method of calculating the eigenvalues $\lambda 1$, $\lambda 2$, and $\lambda 3$ of a Hessian matrix has been described above in reference to operation A620 of FIG. 6, a detailed description thereof will be omitted here.

In operation A720, the medical image registering apparatus 130 calculates a vesselness based on the calculated eigenvalues. For example, when extracting the IVC, the medical image registering apparatus 130 performs a vesselness test by applying Equation 8.

$$V = \begin{cases} 1 & \text{if } \lambda_2 > 0, \lambda_3 > 0 \\ \left(1 - e^{-\frac{R_A^2}{2\alpha^2}}\right) e^{-\frac{R_B^2}{2\beta^2}} \left(1 - e^{-\frac{S^2}{2c^2}}\right) & \text{otherwise} \end{cases} \quad \text{[Equation 8]}$$

In Equation 8, $$R_A = \frac{|\lambda_2|}{|\lambda_3|}, \quad R_B = \frac{|\lambda_1|}{\sqrt{|\lambda_2 \lambda_3|}}, \quad S = \sqrt{\lambda_1^2 + \lambda_2^2 + \lambda_3^2},$$

and the calculated eigenvalues $\lambda 1$, $\lambda 2$, and $\lambda 3$ may satisfy $|\lambda_3| \ge |\lambda_2| \ge |\lambda_1|$.

In addition, $\alpha$, $\beta$, and c are parameters which are determined based on the feature of an anatomic object to be extracted. The parameters $\alpha$ and $\beta$ which are used for extracting the IVC may be equal to approximately 0.5 and the parameter c may be equal to approximately 0.25; however, exemplary embodiments are not limited thereto.

Figure 15C:
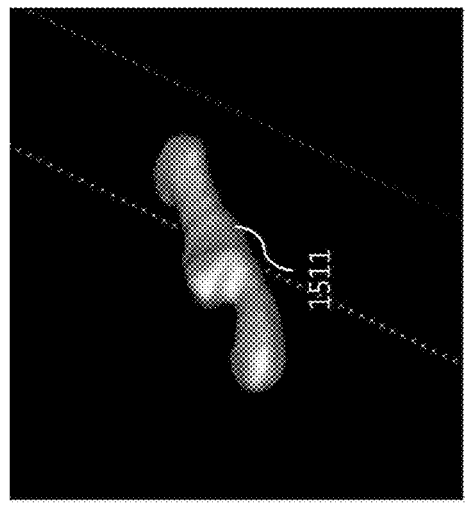
Figure 15B:
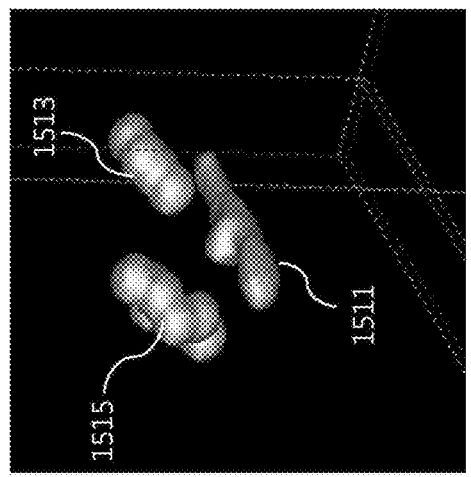
Figure 15A:
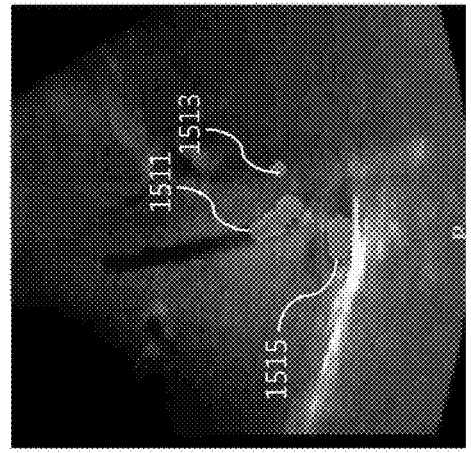

As illustrated in FIGS. 15A and 15B, in operation A725, the medical image registering apparatus 130 may extract one or more IVC candidate regions 1511, 1513, and 1515 which respectively include points at which the calculated vesselness is greater than or equal to a critical value.

FIG. 15B illustrates three-dimensionally rendered images of the extracted IVC candidate regions 1511, 1513, and 1515.

In operation A730, the medical image registering apparatus 130 may calculate a degree of intrinsic IVC quality (hereinafter referred to as an "IVCness") of the one or more extracted IVC candidate regions 1511, 1513, and 1515, and determine the IVC candidate region 1511 which has the greatest IVCness as an IVC region, as illustrated in FIG. 15C.

For example, the IVCness may be calculated based on any one or more of a volume of the IVC candidate region, a distance from the diaphragm, a degree of darkness in comparison with a peripheral region, and a directivity of a center axis with respect to the IVC candidate region. For example, the IVCness may increase as the volume of the IVC candidate region increases, as the distance from the diaphragm decreases, as the degree of darkness in comparison with the peripheral region increases, and/or as the directivity of the center axis with respect to the IVC candidate region is more similar to the direction of the z axis (i.e., the vertical axis of a human body).

Figure 13:
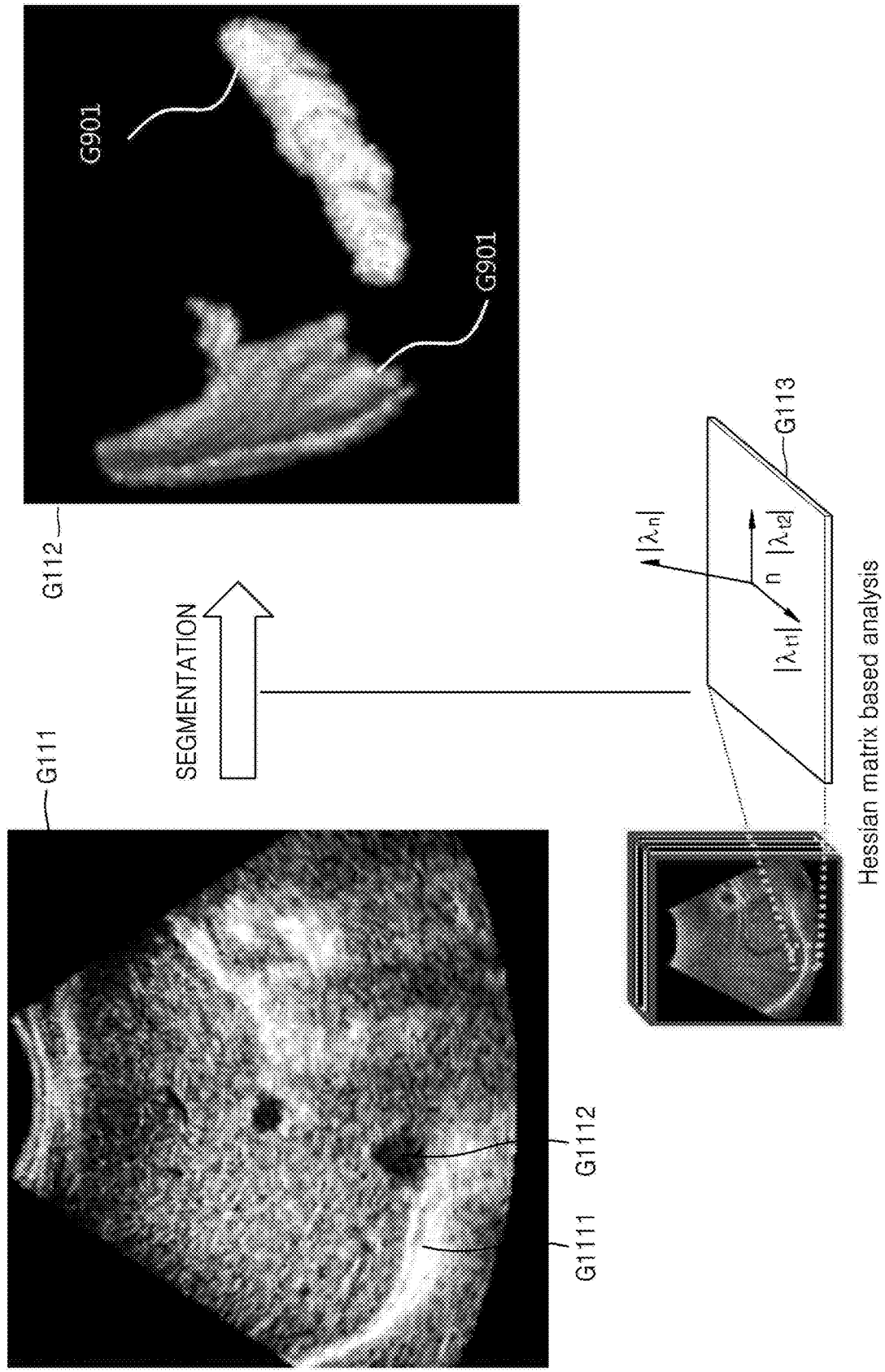

In FIG. 13, G901 in an image G112 represents an extracted diaphragm, and G901 represents an extracted IVC.

Referring to FIG. 3, in operation A325, the medical image registering apparatus 130 registers the first medical image and the second medical image based on a geometric relation between the anatomic objects extracted from the first medical image and the second medical image. A more detailed exemplary embodiment of operation A325 will be described below with reference to FIGS. 8 and 9.

Figure 8:
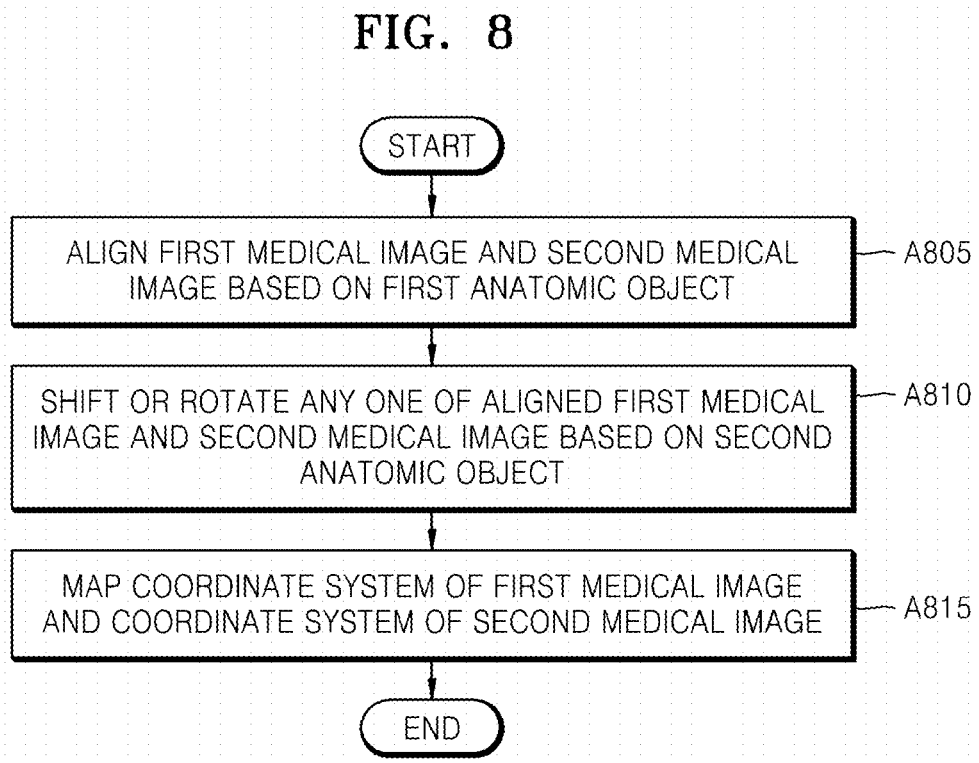
FIG. 8 is a flowchart which illustrates a method for mapping coordinate systems of medical images, according to an exemplary embodiment.
Figure 16:
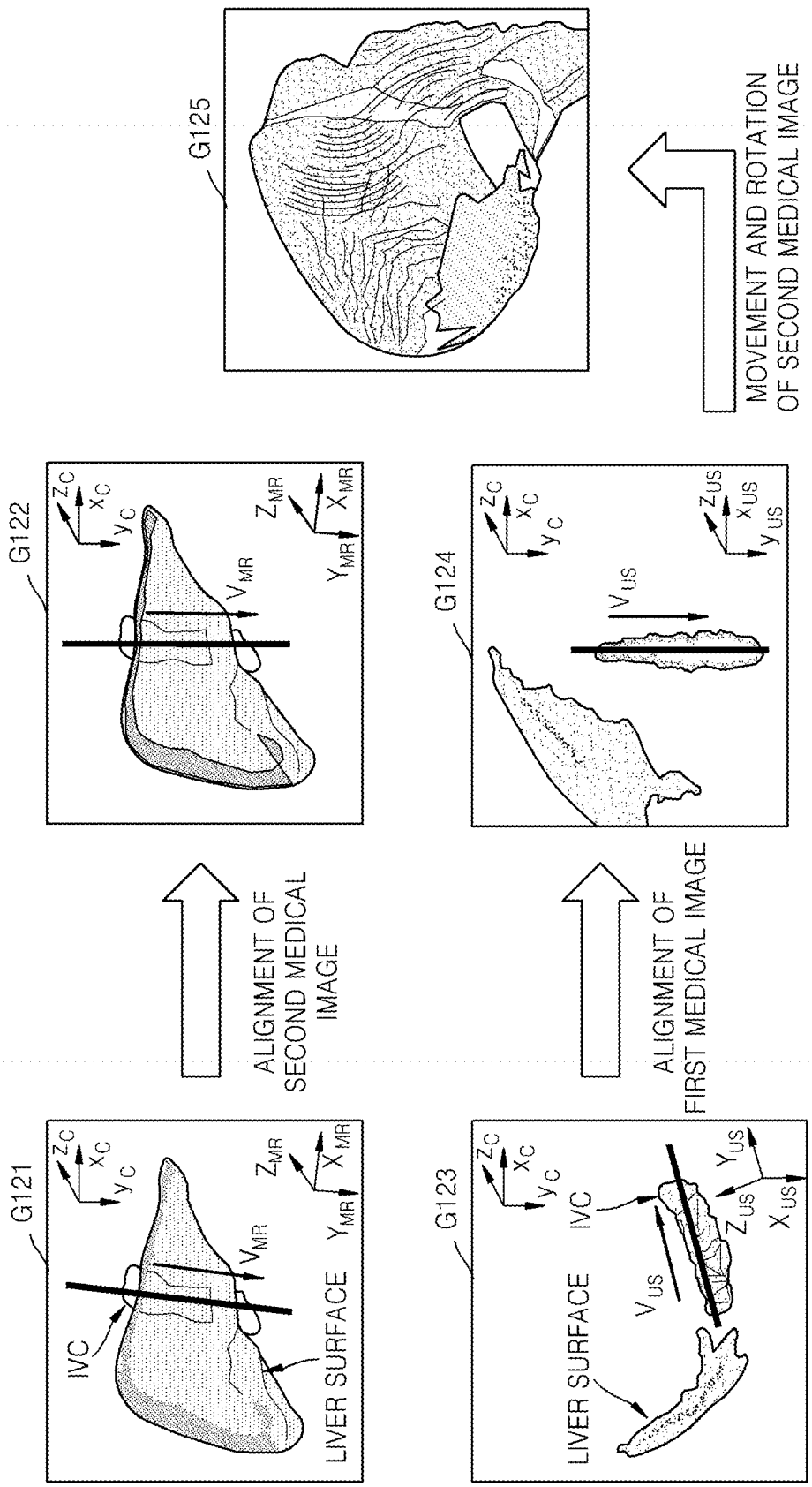

Referring to FIG. 8, in operation A805, the medical image registering apparatus 130 aligns the first medical image and the second medical image based on the first anatomic object. Referring to FIG. 16, an image G121 represents an IVC and a liver surface in the first medical image before registration, and an image G123 represents an IVC and a live surface in the second medical image before registration. The liver surface and the diaphragm are extracted from the image G123. However, because the diaphragm and the liver contact each other and the diaphragm is very thin, the diaphragm may be considered as corresponding to the liver surface. A coordinate system ($X_{MR}$, $Y_{MR}$, $Z_{MR}$) at a right bottom portion in the images G121 and G122 represents a first coordinate system used by the first medical device 110. A coordinate system ($X_{US}$, $Y_{US}$, $Z_{US}$) at a right bottom portion in the image G123 represents a second coordinate system used by the second medical device 120.

A coordinate system ($X_c$, $Y_c$, $Z_c$) at a right top portion in the images G121 to G124 represents a third coordinate system used by the medical image registering apparatus 130. The third coordinate system is used to reduce a calculation amount for medical image registration in the medical image registering apparatus 130. According to some exemplary embodiments, the third coordinate system may be omitted. When the third coordinate system is omitted, the medical image registering apparatus 130 may directly map the other coordinate system based on any one of the first coordinate system and the second coordinate system, but the calculation is complicated to some extent.

$V_{MR}$ in the images G121 and G122 is a vector which represents the position and direction of the IVC in the first coordinate system. $V_{US}$ in the images G123 and G124 is a vector which represents the position and direction of the IVC in the second coordinate system.

The medical image registering apparatus 130 aligns the first medical image based on the first anatomic object. Thereafter, the medical image registering apparatus 130 aligns the second medical image such that the third anatomic object is arranged in the same direction as the first anatomic object.

Referring to FIG. 16, the medical image registering apparatus 130 aligns the first medical image such that the vector $V_{MR}$ in the image G121 is parallel to the $Y_c$ direction of the third coordinate system. G122 represents an aligned first medical image. Likewise, the medical image registering apparatus 130 aligns the second medical image such that the vector $V_{US}$ is parallel to the $Y_c$ direction of the third coordinate system. The medical image registering apparatus 130 may align the second medical image such that the vectors $V_{US}$ and $V_{MR}$ are located in the same space. For example, when the vectors $V_{US}$ and $V_{MR}$ are represented by third coordinate system values, the second medical image may be aligned such that the vectors $V_{US}$ and $V_{MR}$ are present on one straight line and overlap each other. Therefore, it may be understood that a central axis of the IVC is aligned in both of the first medical image and the second medical image.

When the first medical image and the second medical image are aligned in operation A805, the position of the IVC is aligned. However, except for the case where the liver surface is aligned accidentally, the position of the liver surface is not aligned in the first medical image and the second medical image.

In operation A810, the medical image registering apparatus 130 shifts and/or rotates the first medical image or the second medical image based on the second anatomic object. In the following description, for the convenience of description, it is assumed that only the second medical image is rotated and/or shifted.

For example, the liver surface in the image G124 of FIG. 16 and the liver surface in the image G122 are not aligned with each other. In order to align the two liver surfaces with each other, the second medical image needs to be rotated and/or shifted. However, the second medical image may be shifted and/or rotated in operation A805 such that the alignment based on the IVC is preserved. When the second medical image is shifted only in $Y_c$ direction or is rotated only about the $Y_c$ axis, the alignment result in operation A705 may be maintained. In another exemplary embodiment, the magnitude of the shift of the second medical image in the $Z_c$ and $X_c$ directions may be restricted within a predetermined range, and/or the rotation of the second medical image around the $Z_c$ and $X_c$ axes may be restricted within a predetermined angle. In operation A815, the coordinate system of the first medical image is mapped to the coordinate system of the second medical image. An exemplary embodiment of aligning the liver surface in the image G124 and the liver surface in the image G122 with each other will be described below with reference to FIG. 9.

Referring to FIG. 9, in operation A905, the medical image registering apparatus 130 calculates an average of the Euclidian distance from each point of the fourth anatomic object of the second medical image to the most adjacent point of the second anatomic object of the first medical image. For example, the medical image registering apparatus 130 calculates coordinate system values $[M_1, M_2, \ldots, M_N]$ of the third coordinate system for each of N points which are present on the liver surface of the image G122. Likewise, the medical image registering apparatus 130 calculates coordinate system values $[U_1, U_2, \ldots, U_K]$ of the third coordinate system for each of K points which are present on the liver surface of the image G124. The medical image registering apparatus 130 calculates a distance $D_k$ of a point $M_n$ (0<n<N+1, n: integer) that is closest to $U_K$ (0<k<K+1, i: integer).

The medical image registering apparatus 130 adds and averages the calculated distances $D_k$ as expressed in Equation 9.

$$DA = \frac{\sum_{k=1}^{K} D_k}{K} \quad \text{[Equation 9]}$$

Then, in operation A910, the medical image registering apparatus 130 determines whether a calculated average value DA is smaller than or equal to a critical value. For example, when the average value DA is 0, it may be understood that the liver surface in the image G124 and the liver surface in the image G122 are accurately aligned with each other. Herein, the critical value is related to the accuracy of registration, and may be set by the user. For example, when more accurate registration is necessary, the critical value may be decreased, and when more rapid registration is necessary, the critical value may be increased.

When the calculated average value DA is greater than the critical value, in operation A915, the medical image registering apparatus 130 shifts and/or rotates the second medical image to reduce the calculated average value DA. Herein, the direction of reduction of the calculated average value DA may be determined based on the calculated $[M_1, M_2, \ldots, M_N]$ values and $[U_1, U_2, \ldots, U_K]$ values. For example, the direction of the shift and/or rotation of the second medical image may be determined based on vectors, which orient toward a point Mn that is closest to a point Ui, or the sum of the vectors. However, as described above, the second medical image should be rotated and/or shifted such that the axis of the IVC of the second medical image does not deviate from the axis of the IVC of the first medical image, even after the rotation and/or shift of the second medical image.

When the calculated average value DA is smaller than or equal to the critical value, in operation A920, the medical image registering apparatus 130 calculates a function which is usable for transforming the coordinates of the original second medical image into the coordinates of the current second medical image. For example, it is assumed that the image G123 is the original second medical image, and the image G124 is the second medical image when the calculated average value DA is smaller than or equal to the critical value. When the coordinate values of the third coordinate system for each of a start point S, a center point C and an end point E of the IVC in the image G123 are respectively denoted as P1, P2, and P3 and the coordinate values of the third coordinate system for each of a start point S, a center point C and an end point E of the IVC in the image G124 are respectively denoted as P'1, P'2, and P'3, the medical image registering apparatus 130 calculates a coordinate transform function for transforming the P1, P2, and P3 coordinates into the P'1, P'2, and P'3 coordinates. The points S, C and E of the IVC are merely an example for the convenience of description, and exemplary embodiments are not limited thereto. The calculated coordinate transform function may be modified to correspond to the original first medical image G121. In particular, because the image G121 is aligned with the image G122, a change in the coordinate value may be reflected in the coordinate transform function. Accordingly, the coordinate system of the second medical image may be mapped to the coordinate system of the first medical image.

In another exemplary embodiment, when the image G121 is aligned with the image G122, a coordinate change of the first medical image is +Δx, y, z and the calculated average value DA is smaller than or equal to the critical value, the second medical image is rotated and/or shifted by +Δx, y, z. In particular, the second medical image is rotated and/or shifted by +Δx, y, z such that the second medical image corresponds to the original first medical image before the alignment. Thereafter, the medical image registering apparatus 130 calculates a coordinate transform function for transforming the coordinates of the original second medical image into the coordinates of the second medical image that has been rotated and/or shifted by −Δx, y, z.

The process of rotating and/or shifting the second medical image based on the first medical image has been described above. However, those of ordinary skill in the art will understand that the first medical image may be rotated and/or shifted based on the second medical image.

By using the coordinate transform function, the medical image registering apparatus 130 outputs an image which is obtained by registering the first medical image and the second medical image that change in real time. Referring to FIG. 16, an image G125 is an image that renders the result of the registration of the first medical image and the second medical image. The image G125 has the same view as the image G123.

For example, when the probe 121 is shifted, the second medical image changes in real time. In this case, by using the coordinate transform function, the medical image registering apparatus 130 registers the first medical image, which corresponds to the second medical image that changes in real time, to the second medical image. The registered image may be output based on the view of the second medical image.

According to an exemplary embodiment, a sensor which is configured for sensing the position of the probe 121 may be included in the probe 121, or a marker may be attached to a target object in order to sense the position of the probe 121. According to another exemplary embodiment, the sensor or marker for sensing the position of the probe 121 may be omitted. For example, the movement of the probe 121 may be detected by comparing the previous frame and the current frame of the second medical image.

As described above, according to the one or more of the above-described exemplary embodiments, the non-real-time medical image and the real-time medical image may be registered rapidly and accurately, and the user's intervention for registering may be minimized.

In addition, other exemplary embodiments may also be implemented through computer-readable code/instructions in/on a medium, e.g., a transitory or non-transitory computer-readable medium, to control at least one processing element to implement any above-described exemplary embodiment. The medium may correspond to any medium/media permitting the storage and/or transmission of the computer-readable code.

The computer-readable code may be recorded/transferred on a medium in a variety of ways, with examples of the medium including recording media, such as magnetic storage media (e.g., ROM, floppy disks, hard disks, etc.) and optical recording media (e.g., CD-ROMs, or DVDs), and transmission media such as Internet transmission media. Thus, the medium may be such a defined and measurable structure including or carrying a signal or information, such as a device carrying a bitstream according to one or more exemplary embodiments. The media may also be a distributed network, so that the computer-readable code is stored/transferred and executed in a distributed fashion. Furthermore, the processing element may include a processor or a computer processor, and processing elements may be distributed and/or included in a single device.

It should be understood that the exemplary embodiments described therein should be considered in a descriptive sense only and not for purposes of limitation. Descriptions of features or aspects within each exemplary embodiment should typically be considered as available for other similar features or aspects in other exemplary embodiments.

While one or more exemplary embodiments have been described with reference to the figures, it will be understood by those of ordinary skill in the art that various changes in form and details may be made therein without departing from the spirit and scope of the present inventive concept as defined by the following claims.

What is claimed is:

1. A method for registering medical images of different types, the method comprising:
   receiving a selection of at least one point from within a first medical image, wherein the first medical image is acquired in non-real time;
   extracting, from the first medical image, a first anatomic object which includes the selected point and a second anatomic object which is adjacent to the selected point;
   acquiring, in real time, by a medical image acquisition device, a second medical image;
   extracting, from the second medical image that is acquired in real time, a third anatomic object which corresponds to the first anatomic object and a fourth anatomic object which corresponds to the second anatomic object; and
   registering the first medical image and the second medical image,
   wherein the registering the first medical image and the second medical image comprises aligning the first medical image and the second medical image with respect to an axis, based on the first anatomic object and the third anatomic object, and shifting any one of the aligned first medical image and the aligned second medical image along the axis, based on the second anatomic object and the fourth anatomic object,
   wherein the first anatomic object and the third anatomic object are an inferior vena cava (IVC), the second anatomic object is a liver, and the fourth anatomic object is a diaphragm, and
   wherein the extracting the second anatomic object comprises:
   detecting, in the first medical image that is contrast-enhanced, at least two candidate points which have brightness values that fall within a predetermined brightness value range;
   calculating a probability that the detected at least two candidate points will be in the second anatomic object;
   forming at least one cluster which is constructed by points at which the calculated probability is greater than or equal to a predetermined critical value; and
   determining one of the at least one cluster as a region of the second anatomic object.

2. The method of claim 1, wherein the extracting the first anatomic object comprises:
   detecting at least two points that are adjacent to the selected point and which have an anatomic feature which is similar to an anatomic feature of the selected point; and determining a region of the first anatomic object by using the detected points.

3. The method of claim 2, wherein the detecting the at least two points which have the anatomic feature which is similar to the anatomic feature of the selected point comprises detecting at least two points which have a contrast that is smaller than or equal to a predetermined value with respect to the selected point, in the first medical image that is contrast-enhanced.

4. The method of claim 1, wherein the determining the one of the at least one cluster as the region of the second anatomic object comprises determining a cluster which has a maximum volume from among the at least one cluster as the determined region.

5. The method of claim 1, wherein the determining the one of the at least one cluster as the region of the second anatomic object comprises:
   calculating an average probability that points included in each cluster from among the at least one cluster are included in the region of the second anatomic object; and
   determining the cluster which has a maximum calculated average probability from among the at least one cluster as the region of the second anatomic object.

6. The method of claim 1, wherein the receiving the selection of the at least one point comprises receiving a selection of at least one point for which a brightness value does not fall within the predetermined brightness value range.

7. The method of claim 1, wherein the extracting the third and fourth anatomic objects comprises:
   generating a binarized image of the second medical image based on a brightness value of the second medical image;
   calculating eigenvalues of a Hessian matrix at respective candidate points of the binarized image; and
   determining, based on the calculated eigenvalues, whether the respective candidate points of the binarized image are included in at least one from among the third anatomic object and the fourth anatomic object.

8. The method of claim 7, wherein the generating the binarized image of the second medical image comprises:
   determining a critical brightness value based on at least one ultrasound reflection characteristic of at least one from among the third anatomic object and the fourth anatomic object; and
   binarizing the second medical image by using the critical brightness value.

9. The method of claim 7, wherein the determining whether the respective candidate points of the binarized image are included in the at least one from among the third anatomic object and the fourth anatomic object comprises:
   calculating a respective flatness of each of the respective candidate points based on the calculated eigenvalues; and
   determining, based on the calculated flatness, whether each of the respective candidate points is included in at least one from among the third anatomic object and the fourth anatomic object.

10. The method of claim 1, wherein the extracting the third anatomic object and the fourth anatomic object from the second medical image comprises:
    extracting a boundary of the third anatomic object;
    determining points which are located within a predetermined distance from the extracted boundary as candidate points;
    calculating eigenvalues of a Hessian matrix at the candidate points; and
    determining, based on the calculated eigenvalues, whether each of the candidate points is included in the fourth anatomic object.

11. The method of claim 1, wherein the registering the first medical image and the second medical image further comprises mapping a coordinate system of the shifted image to a coordinate system of the image that has not been shifted.

12. The method of claim 1, wherein the first medical image includes one from among a three-dimensional (3D) magnetic resonance (MR) image, a computed tomography (CT) image, a positron emission tomography (PET) image, a single positron emission computed tomography (SPECT) image, and an X-ray image that is captured prior to a medical treatment, and
    wherein the second medical image includes one from among a two-dimensional (2D) ultrasound image that is captured in real time during the medical treatment and a 3D ultrasound image that is captured in real time during the medical treatment.

13. A non-transitory computer-readable recording medium that stores a program which, when executed by a computer, performs the method of claim 1.

14. An apparatus for registering medical images of different types, the apparatus comprising:
    a storage device configured to store a first medical image that is acquired in non-real time;
    a user interface configured to output the stored first medical image and to receive a selection of at least one point from within the first medical image;
    a medical image acquisition device configured to acquire, in real time, a second medical image of a different type from the first medical image; and
    an image processor configured to:
      extract, from the first medical image, a first anatomic object which includes the selected point and a second anatomic object which is adjacent to the selected point;
      extract, from the second medical image, a third anatomic object which corresponds to the first anatomic object and a fourth anatomic object which corresponds to the second anatomic object; and
      register the first medical image and the second medical image,
    wherein the image processor registers the first medical image and the second medical image by aligning the first medical image and the second medical image with respect to an axis, based on the first anatomic object and the third anatomic object, and shifts any one of the aligned first medical image and the aligned second medical image along the axis, based on the second anatomic object and the fourth anatomic object,
    wherein the first anatomic object and the third anatomic object are an inferior vena cava (IVC), the second anatomic object is a liver, and the fourth anatomic object is a diaphragm, and
    wherein the image processor is further configured to:
    detect, in the first medical image that is contrast-enhanced, at least two candidate points which have brightness values that fall within a predetermined brightness value range;
    calculate a probability that the detected at least two candidate points will be in the second anatomic object;
    form at least one cluster which is constructed by points at which the calculated probability is greater than or equal to a predetermined critical value; and determine one of the at least one cluster as a region of the second anatomic object.

15. The apparatus of claim 14, wherein the image processor is further configured to detect at least two points that are adjacent to the selected point and which have an anatomic feature which is similar to an anatomic feature of the selected point, and to determine a region of the first anatomic object which includes the selected point by using the detected at least two points, and wherein the detected points have a contrast that is smaller than or equal to a predetermined value with respect to the selected point, in the first medical image that is contrast-enhanced, in order to detect the at least two points which have the anatomic feature which is similar to the anatomic feature of the selected point.

16. The apparatus of claim 14,
wherein a brightness value of the selected point in the first medical image does not fall within the predetermined brightness value range.

17. The apparatus of claim 16, wherein the image processor is further configured to determine a cluster which has a maximum volume among the at least one cluster as the determined region of the second anatomic object.

18. The apparatus of claim 16, wherein the image processor is further configured to calculate an average probability that points included in each of the at least one cluster are included in the region of the second anatomic object; and to determine a cluster which has a maximum average probability from among the at least one cluster as the determined region of the second anatomic object.

19. The apparatus of claim 14, wherein the image processor is further configured to:

generate a binarized image of the second medical image based on a brightness value of the second medical image;

calculate eigenvalues of a Hessian matrix at respective candidate points of the binarized image; and determine, based on the calculated eigenvalues, whether the respective candidate points of the binarized image are included in at least one from among the third anatomic object and the fourth anatomic object.

20. The apparatus of claim 19, wherein the image processor is further configured to determine a critical brightness value based on at least one ultrasound reflection characteristic of at least one from among the third anatomic object and the fourth anatomic object, and binarize the second medical image by using the determined critical brightness value.

21. The apparatus of claim 19, wherein the image processor is further configured to calculate a respective flatness of each of the respective candidate points of the binarized image based on the calculated eigenvalues, and determine, based on the calculated flatness, whether each of the respective candidate points is included in at least one from among the third anatomic object and the fourth anatomic object.

22. The apparatus of claim 14, wherein the image processor is further configured to extract a boundary of the third anatomic object; determine points which are located within a predetermined distance from the extracted boundary as candidate points; calculate eigenvalues of a Hessian matrix at the candidate points; and determine, based on the calculated eigenvalues, whether each of the candidate points is included in at least one from among the third anatomic object and the fourth anatomic object.

23. The apparatus of claim 14, wherein the image processor is further configured to map a coordinate system of the shifted image to a coordinate system of the image that has not been shifted.

* * * * *